United States Patent
Nishino et al.

(10) Patent No.: US 9,513,379 B2
(45) Date of Patent: Dec. 6, 2016

(54) RADIOGRAPHIC IMAGE CAPTURE DEVICE, SYSTEM, PROGRAM STORAGE MEDIUM AND METHOD

(75) Inventors: Naoyuki Nishino, Kanagawa (JP); Naoto Iwakiri, Kanagawa (JP); Haruyasu Nakatsugawa, Kanagawa (JP); Yasunori Ohta, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 272 days.

(21) Appl. No.: 13/596,750

(22) Filed: Aug. 28, 2012

(65) Prior Publication Data

US 2013/0075620 A1    Mar. 28, 2013

(30) Foreign Application Priority Data

Sep. 27, 2011    (JP) ................................ 2011-211355

(51) Int. Cl.
*G01T 1/20* (2006.01)
*A61B 6/00* (2006.01)

(52) U.S. Cl.
CPC ............. *G01T 1/2018* (2013.01); *A61B 6/548* (2013.01)

(58) Field of Classification Search
None
See application file for complete search history.

(56) References Cited

U.S. PATENT DOCUMENTS

| | | | | |
|---|---|---|---|---|
| 5,554,849 A | * | 9/1996 | Gates | ....................... 250/370.08 |
| 6,643,411 B2 | * | 11/2003 | Nonaka | ................... H01L 27/00 |
| | | | | 257/E27.001 |
| 6,849,853 B2 | * | 2/2005 | Ikeda et al. | .............. 250/370.09 |
| 6,952,015 B2 | * | 10/2005 | Kameshima | .......... G01T 1/2018 |
| | | | | 250/363.07 |
| 7,368,724 B2 | * | 5/2008 | Morii et al. | ............. 250/370.01 |
| 7,592,577 B1 | * | 9/2009 | Liu | ............................ 250/208.1 |

(Continued)

FOREIGN PATENT DOCUMENTS

| | | |
|---|---|---|
| JP | 2009-032854 | 2/2009 |
| JP | 4217443 | 2/2009 |

(Continued)

OTHER PUBLICATIONS

Nikkei Newspaper article published online (Nov. 8, 2010), "The University of Tokyo develops Ultra-flexible Organic Transistor", Internet <URL: http://www.nikkei.com/tech/trend/article/g=96958A9C93819499E2EAE2E0E48DE2EAE3E3E0E2E3E2E2E2E2E2E2; p=9694E0E7E2E6E0E2E3E2E2E0E2E0>.

*Primary Examiner* — David Porta
*Assistant Examiner* — Blake Riddick
(74) *Attorney, Agent, or Firm* — Young & Thompson

(57) ABSTRACT

A radiographic image capture device includes a radiation detector, an application section and a controller. The radiation detector includes plural detection pixels that detect a radiation application state and plural imaging pixels that capture a radiographic image. The application section applies a bias voltage to each of the plural detection pixels and to each of the plural imaging pixels. The controller effects control such that, if the radiation application amount detected by the detection pixels is equal to or greater than a first threshold value during a first state in which the bias voltage is applied to the plural detection pixels, the application section is caused to transition to a second state in which the bias voltage applied to the detection pixels is reduced.

28 Claims, 19 Drawing Sheets

(56) References Cited

U.S. PATENT DOCUMENTS

| | | | |
|---|---|---|---|
| 7,638,773 B2* | 12/2009 | Kuwabara | G03B 42/04 250/370.08 |
| 7,768,002 B2* | 8/2010 | Kitamura et al. | 257/40 |
| 8,705,700 B2* | 4/2014 | Eguchi | 378/116 |
| 9,366,766 B2* | 6/2016 | Okada | G01T 1/2018 |
| 2001/0012070 A1* | 8/2001 | Enod | H04N 5/32 348/302 |
| 2003/0038242 A1* | 2/2003 | Endo | H01L 27/14603 250/370.14 |
| 2003/0213915 A1* | 11/2003 | Chao et al. | 250/370.14 |
| 2005/0178749 A1* | 8/2005 | Yamazaki et al. | 219/121.62 |
| 2007/0069142 A1* | 3/2007 | Moody et al. | 250/370.09 |
| 2007/0131843 A1* | 6/2007 | Yokoyama | H04N 5/32 250/205 |
| 2007/0176109 A1* | 8/2007 | Bell | 250/370.09 |
| 2007/0210258 A1* | 9/2007 | Endo | H04N 5/32 250/370.09 |
| 2008/0203309 A1* | 8/2008 | Frach et al. | 250/362 |
| 2009/0026379 A1* | 1/2009 | Yaegashi et al. | 250/370.09 |
| 2009/0224162 A1* | 9/2009 | Inuiya et al. | 250/370.09 |
| 2009/0224235 A1* | 9/2009 | Kitamura et al. | 257/40 |
| 2009/0250592 A1* | 10/2009 | Takeda et al. | 250/205 |
| 2010/0084564 A1* | 4/2010 | Moody et al. | 250/366 |
| 2010/0252723 A1* | 10/2010 | Frach et al. | 250/252.1 |
| 2011/0001053 A1* | 1/2011 | Solf | 250/370.08 |
| 2012/0087472 A1* | 4/2012 | Nyholm | H04N 5/23238 378/62 |
| 2013/0009069 A1* | 1/2013 | Okada | G01T 1/243 250/370.09 |
| 2013/0126742 A1* | 5/2013 | Hayun et al. | 250/366 |
| 2015/0316661 A1* | 11/2015 | Fujiyoshi | G01T 1/2018 378/62 |

FOREIGN PATENT DOCUMENTS

| | | |
|---|---|---|
| JP | 4217506 | 2/2009 |
| JP | 2009-212377 | 9/2009 |
| JP | 2009-212389 | 9/2009 |

* cited by examiner

FIG.12

CAPTURE INFORMATION INPUT SCREEN

PLEASE INPUT SUBJECT NAME, IMAGING TARGET SITE,
IMAGING POSTURE AND EXPOSURE CONDITIONS.

NAME

IMAGING TARGET SITE

IMAGING POSTURE

EXPOSURE CONDITIONS
　　　TUBE VOLTAGE
　　　TUBE CURRENT

INPUT COMPLETE

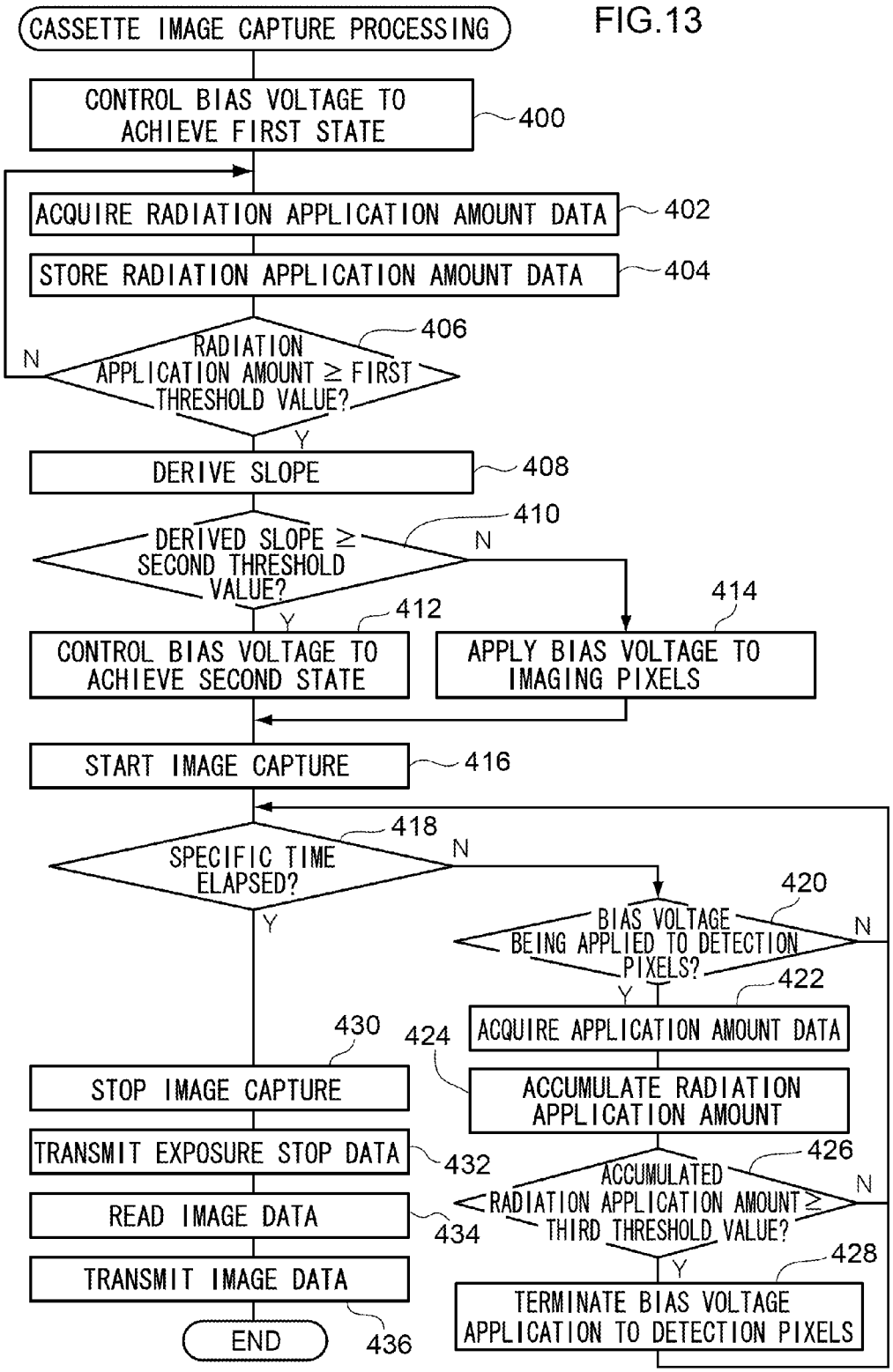

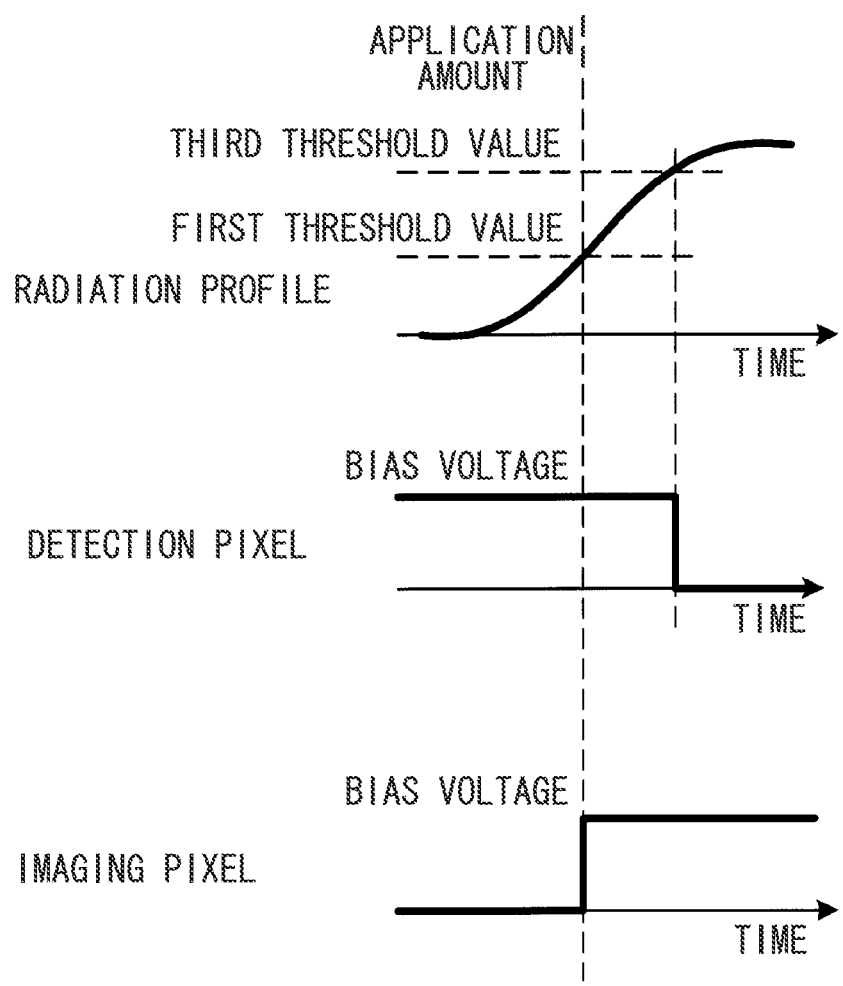

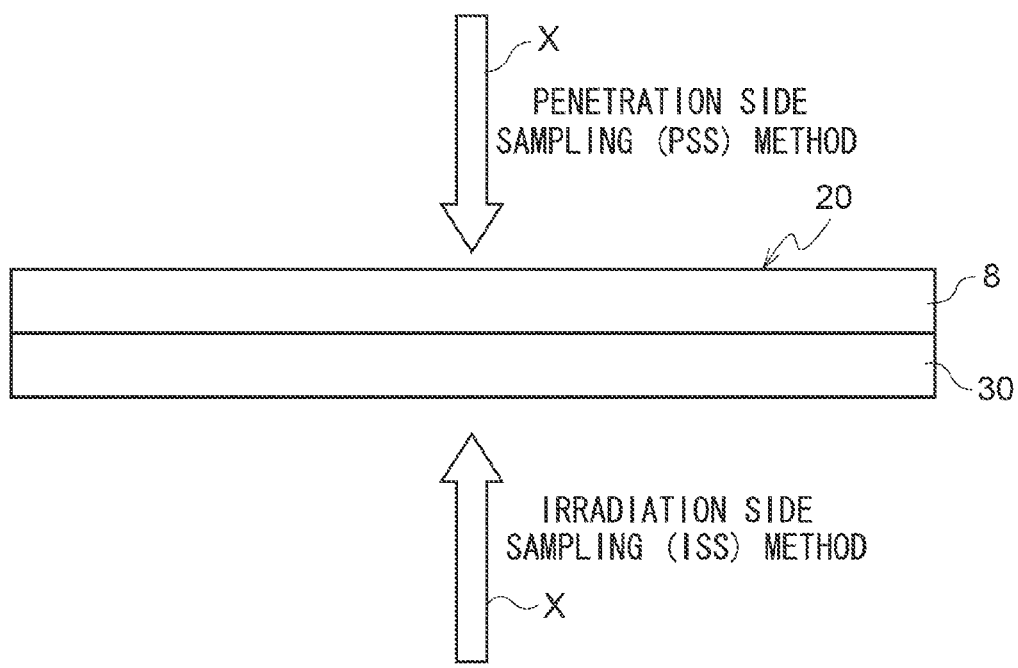

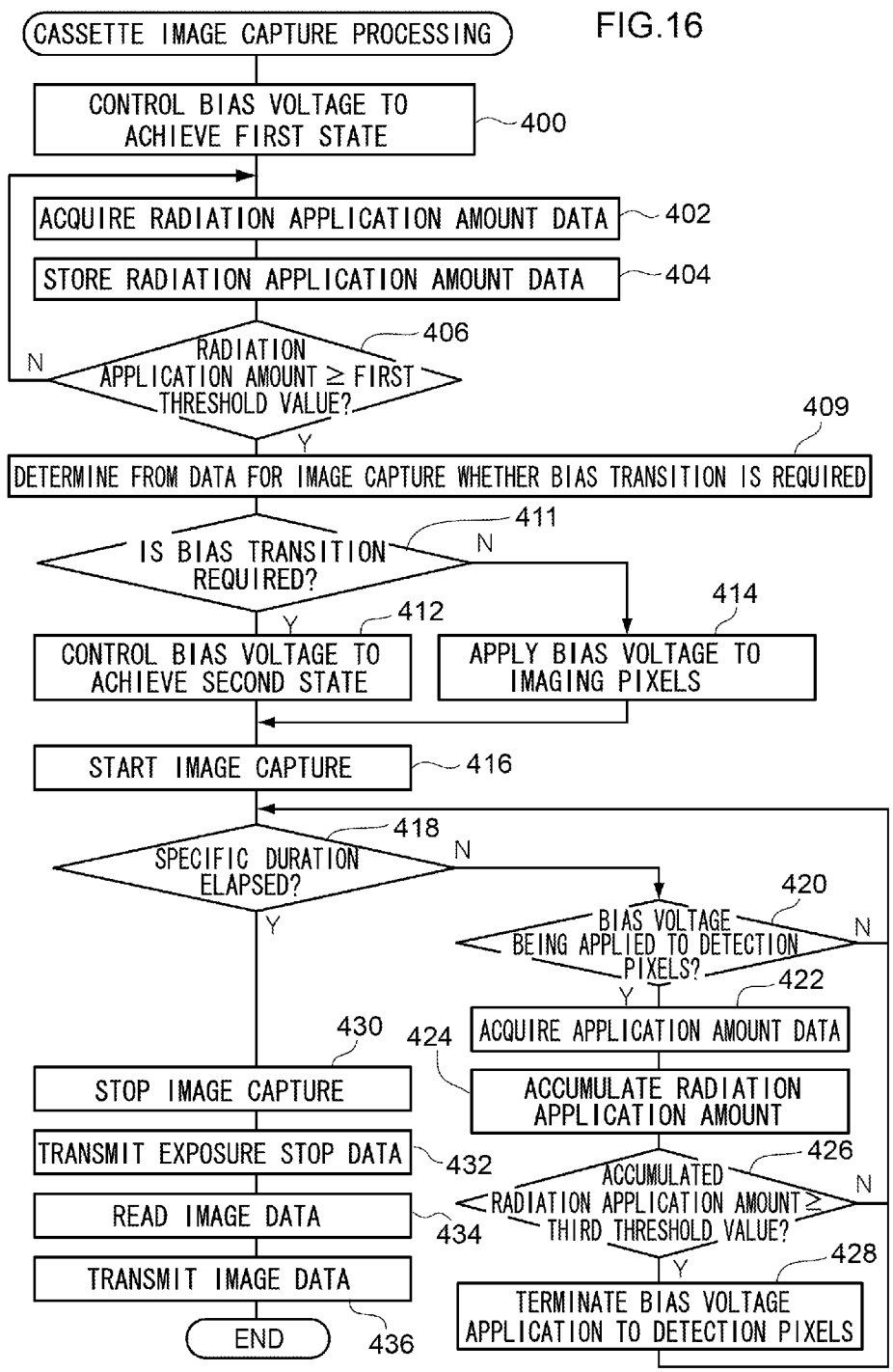

RADIOGRAPHIC IMAGE CAPTURE DEVICE, SYSTEM, PROGRAM STORAGE MEDIUM AND METHOD

CROSS-REFERENCE TO RELATED APPLICATION

This application claims priority under 35 USC 119 from Japanese Patent Application No. 2011-211355, filed on Sep. 27, 2011, the disclosure of which is incorporated by reference herein.

BACKGROUND OF THE INVENTION

Field of the Invention

The present invention relates to a radiographic image capture device, system, program storage medium and method, and in particular to a radiographic image capture device, system, program storage medium and method that captures a radiographic image expressing radiation passed through an imaging target site.

Description of the Related Art

Recently, radiation detectors such as Flat Panel Detectors (FPDs) are being implemented in which a radiation sensitive layer is disposed on a Thin Film Transistor (TFT) active matrix substrate and with which radiation can be converted directly into digital data. Radiographic image capture devices that employ such radiation detectors and can capture radiographic images expressing irradiated radiation are also being implemented. Radiation conversion methods used by radiation detectors employed in such radiographic image capture devices include indirect conversion methods, in which radiation is first converted into light with a scintillator and then the converted light is converted into electric charge with a semiconductor layer such as a photodiode, or direct conversion methods in which radiation is converted into electric charge with a semiconductor layer such as amorphous selenium. There are various materials that may be used in the semiconductor layer for each method.

In such radiographic image capture devices, if the radiographic image capture device itself can detect states such as initiation of radiation application, termination of radiation application, and an amount of radiation application, it becomes unnecessary to connect an image capture control device (referred to as a console) that performs overall control of the radiographic image capture device and the radiation source to the radiation source. Such a configuration is preferable from the perspective of simplifying the system configuration and simplifying control by the image capture control device.

An example of such technology related to radiographic image capture devices that can detect states of radiation application is disclosed in Japanese Patent No. 4217443. This radiographic image capture device includes a pixel area with plural pixels disposed on a substrate. Each pixel includes a phosphor material that converts incident radiation into visible light, a first photoelectric conversion element that converts the visible light into electrical signals, and a switching element that switches the output operations of the electrical signals from the photoelectric conversion element. Image data is generated based on the electrical signals output from the first photoelectric conversion elements. The radiographic image capture device includes a second photoelectric conversion element that detects the amount of incident radiation, and the switching elements and the second photoelectric conversion elements are disposed between the substrate and the first photoelectric conversion elements in the pixel area.

Japanese Patent No. 4217506 discloses a radiation imaging device having a conversion section provided with plural pixels, each having a first conversion element, wherein the conversion section is provided on the side of a substrate on which radiation is incident. The radiation imaging device outputs image data according to the amount of radiation incident to the conversion section. The radiation imaging device includes second conversion elements that detect at least one of a radiation application amount incident to the conversion section, the start and end of incidence of radiation to the conversion section. The second conversion elements are disposed between the first conversion elements of adjacent pixels in the conversion section on the side of the substrate on which radiation is incident. The second conversion elements have a width in one direction that is smaller than the pitch of the pixels.

However, in the above technologies, since the sensors for detecting radiation are embedded between the pixels for image generation, electric charges generated by photoelectric conversion are temporarily accumulated in these sensors. As a result, at least one of charge leakage (blooming) or induction charges due to floating capacitance may occur in the above technology, and this may cause deterioration in captured image quality. Such issues are more significant as the pixel pitch of the radiation detector is smaller.

SUMMARY OF THE INVENTION

The present invention provides a radiographic image capture device, system, program storage medium and method capable of preventing deterioration in quality of captured image, which may be caused by charge accumulated in pixels for radiation detection.

A first aspect of the present invention is a radiographic image capture device including: a radiation detector including plural detection pixels that detect a radiation application state and plural imaging pixels that capture a radiographic image; an application section that applies a bias voltage to each of the plural detection pixels and to each of the plural imaging pixels; and a controller that effects control such that, if the radiation application amount detected by the detection pixels is equal to or greater than a first threshold value during a first state in which the bias voltage is applied to the plural detection pixels, the application section is caused to transition to a second state in which the bias voltage applied to the detection pixels is reduced.

As described above, the radiographic image capture device of the first aspect transitions to the second state in which the bias voltage applied to the detection pixels is lowered when the radiation application amount detected by the detection pixels in the first state in which the bias voltage is applied to the detection pixels becomes the first threshold value or greater. Accordingly, the first aspect may prevent deterioration in image quality, which may be caused by accumulated charges in the detection pixels.

In the above aspect, the first state may be a state in which the bias voltage is applied to the detection pixels and the bias voltage is not applied to the imaging pixels, and the second state may be a state in which the bias voltage applied to the detection pixels is reduced and the bias voltage is applied to the imaging pixels. In this way, it is possible to prevent deterioration in quality of captured image due to eliminating the effects of dark current in the imaging pixels.

In the above aspect, the controller may effect the control if a slope of increase in the radiation application amount detected by the detection pixels in the first state is equal to or greater than a second threshold value. Execution of unnecessary processing may accordingly be avoided.

In the above configuration, the controller may effect the control if the slope of increase in the radiation application amount detected by the detection pixels in the first state is less than the second threshold value and the radiation application amount is equal to or greater than a third threshold value that is greater than the first threshold value. Deterioration in quality of captured image, which may caused by charge accumulation in the detection pixels may accordingly be even more reliably prevented.

In the above aspect, the controller may effect the control based on data for image capture expressing conditions for radiographic image capture. In this way, execution of unnecessary processing may be more easily and effectively avoided than in cases in which the control is effected based on the slope of increase in the radiation application amount.

In the above aspect, the plural detection pixels may be disposed between the plural imaging pixels. The advantage of the first aspect may be readily appreciated in this configuration since blooming and induction charges due to floating capacitance are prone to occur in this configuration.

In the above aspect, each of the plural detection pixels may be formed by adding a radiation detection thin-film transistor to one of the plural imaging pixels.

In the above aspect, the plural detection pixels may be respectively formed in some of the plural imaging pixels by dividing a region of a sensor portion of each imaging pixel to serve as a radiation application state detection region.

In the above aspect, the second state may be one of the following states:

(a) a state in which a second bias voltage is applied to the plural detection pixels, wherein the second bias voltage is lower than the bias voltage and higher than a voltage applied to the plural detection pixels in a state in which the bias voltage is not applied;

(b) a state in which the bias voltage is not applied to the detection pixels; or (c) a state in which a third bias voltage that has a reverse polarity with respect to the bias voltage is applied to the detection pixels.

If the second state is (b), that is the state in which the bias voltage is not applied to the detection pixels, the application section may further include a power supply section that generates the bias voltage that is common for the plural detection pixels and the plural imaging pixels, and a switching section that selectively switches a feed-destination of the bias voltage generated by the power supply section to the plural detection pixels or the plural imaging pixels; and the controller may causes transition from the first state to the second state by switching of the switching section. A radiation detector may accordingly be realized at lower cost and with more economical use of space than in cases in which separate application sections are provided for both the detection pixels and the imaging pixels.

A second aspect of the present invention is a radiographic image capture system including: a radiographic image capture device including a radiation detector including plural detection pixels that detect a radiation application state and plural imaging pixels that capture a radiographic image, and an application section that applies a bias voltage to each of the plural detection pixels and to each of the plural imaging pixels; and a controller that effects control such that, if the radiation application amount detected by the plural detection pixels is equal to or greater than a first threshold value during a first state in which the bias voltage is applied to the detection pixels, the application section is caused to transition to a second state in which the bias voltage applied to the detection pixels is reduced.

As described above, the radiographic image capture system of the second aspect effects control of transitioning to the second state in which the bias voltage applied to the detection pixels is lowered when the radiation application amount detected by the detection pixels in the first state in which the bias voltage is applied to the detection pixels has become the first threshold value or greater. Accordingly, the second aspect may prevent deterioration in quality of captured image, which may be caused by accumulated charges in the detection pixels.

A third aspect of the present invention is a non-transitory computer readable program storage medium that stores a program that causes a radiographic image capture device to perform a processing, the radiographic image capture device including a radiation detector including plural detection pixels that detect a radiation application state and plural imaging pixels that capture a radiographic image, and an application section that applies a bias voltage to each of the plural detection pixels and to each of the plural imaging pixels, the processing including: determining whether or not the radiation application amount detected by the detection pixels during a first state in which the bias voltage is applied to the detection pixels is equal to or greater than a first threshold value; and controlling the application section to transition to a second state in which the bias voltage applied to the detection pixels is reduced if it is determined that the application amount is equal to or greater than the first threshold.

Since the program of the third aspect causes a computer to operate similarly as in the first aspect, it is also capable of preventing deterioration in quality of captured image, which may be caused by accumulated charges in the detection pixels.

A fourth aspect of the present invention is a radiographic image capture method for a radiation detector including plural detection pixels that detect a radiation application state and plural imaging pixels that capture a radiographic image, the method including: determining whether or not a radiation application amount detected by the plural detection pixels during a first state, in which a bias voltage is applied to the plural detection pixels, is equal to or greater than a first threshold value; and transitioning to a second state in which the bias voltage applied to the plural detection pixels is reduced if it is determined that the application amount is equal to or greater than the first threshold value.

Since the operation of the fourth aspect is similar to that of the first aspect, it is also capable of preventing deterioration in quality of captured image, which may be caused by accumulated charges in the detection pixels.

According to the above aspects, it is capable of preventing deterioration in captured image quality caused by accumulated charges in the detection pixels by effecting control of transitioning to the second state in which the bias voltage applied to the detection pixels is lowered when the radiation application amount detected by the detection pixels in the first state in which the bias voltage is applied to the detection pixels becomes the first threshold value or greater.

BRIEF DESCRIPTION OF THE DRAWINGS

Exemplary embodiments of the present invention will be described in detail based on the following figures, wherein:

FIG. 12 is a schematic diagram illustrating an example of a capture information input screen according to exemplary embodiments;

FIG. 13 is a flow chart illustrating flow of processing in a cassette image capture program according to a first exemplary embodiment;

FIG. 14 is a waveform diagram for explanation of the bias switching function;

FIG. 15 is a cross-sectional side view for explaining radiographic imaging using an Irradiation Side Sampling (ISS) method and a Penetration Side Sampling (PSS) method;

FIG. 16 is a flow chart illustrating flow of processing of a cassette image capture program according to a second exemplary embodiment;

DETAILED DESCRIPTION OF THE INVENTION

Hereinafter, an example of a case in which an embodiment is applied to a radiology information system, which is a system that as a whole manages information handled in a radiology department in a hospital, will be described.

[First Embodiment]

Figure 1:
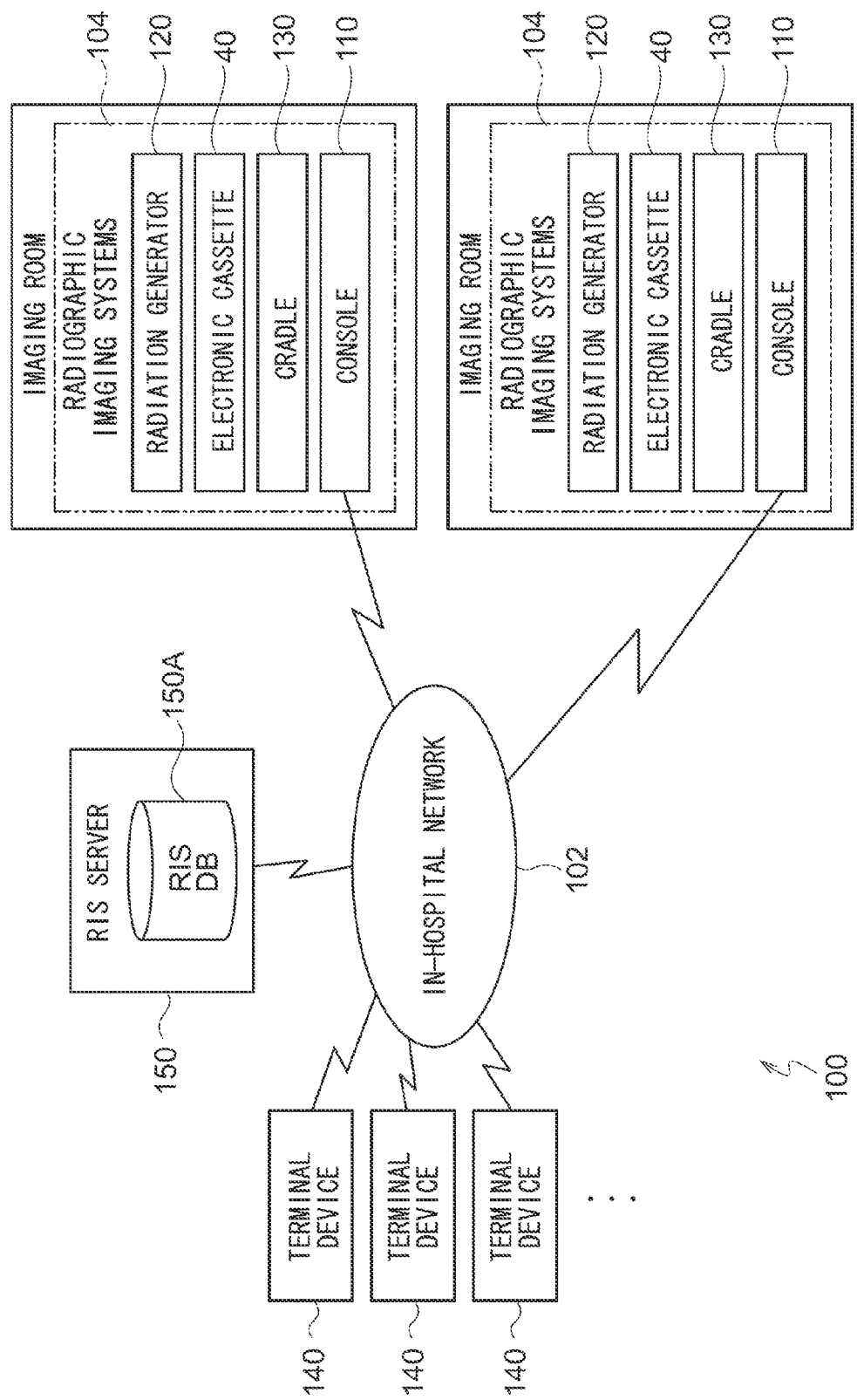
FIG. 1 is a block diagram illustrating a configuration of a radiographic image capture system according to exemplary embodiments.

First, the configuration of a radiology information system (RIS) 100 (hereinafter called "the RIS 100") pertaining to the present exemplary embodiment will be described with reference to FIG. 1.

The RIS 100 is a system for managing information such as medical service appointments and diagnostic records in a radiology department and configures part of a hospital information system (hereinafter called "the HIS").

The RIS 100 has plural imaging request terminal devices 140 (hereinafter called "the terminal device(s) 140"), an RIS server 150, and radiographic image capture systems (hereinafter called "the imaging system(s)" 104). The imaging systems 104 are installed in individual radiographic imaging rooms (or operating rooms) in a hospital. The RIS 100 is configured as a result of the terminal devices 140, the RIS server 150, and the imaging systems 104 being connected to an in-hospital network 102 configured by a wired or wireless local area network (LAN). The RIS 100 configures part of the HIS disposed in the same hospital, and an HIS server (not shown in the drawings) that manages the entire HIS is also connected to the in-hospital network 102.

The terminal devices 140 are for doctors or radiologic technologists to input and browse diagnostic information and facility reservations. Radiographic imaging requests and imaging reservations are also made via the terminal devices 140. Each of the terminal devices 140 includes a personal computer having a display device, and the terminal devices 140 are made capable of intercommunicating with the RIS server 150 via the in-hospital network 102.

The RIS server 150 receives the imaging requests from each of the terminal devices 140 and manages radiographic imaging schedules in the imaging systems 104. The RIS server 150 includes a database 150A.

The database 150A includes: information relating to patients (subjects), such as attribute information (names, sexes, dates of birth, ages, blood types, body weights, patient identifications (IDs), etc.), medical histories, consultation histories, radiographic images that have been captured in the past, etc.; information relating to later-described electronic cassettes 40 used in the imaging systems 104, such as identification numbers (ID information), models, sizes, sensitivities, dates of first use, numbers of times used, etc.; and environment information representing the environments in which radiographic images are captured using the electronic cassettes 40—that is, the environments in which the electronic cassettes 40 are used (e.g., radiographic imaging rooms, operating rooms, etc.).

The imaging systems 104 capture radiographic images as a result of being operated by the doctors or the radiologic technologists in response to an instruction from the RIS server 150. Each of the imaging systems 104 is equipped with a radiation generator 120, an electronic cassette 40, a cradle 130, and a console 110. The radiation generator 120 applies a dose of radiation X (see also FIG. 6) according to exposure conditions from a radiation source 121 (see also FIG. 2) to a subject. The electronic cassette 40 has a built-in radiation detector 20 (see also FIG. 6) that absorbs the radiation X that has passed through an imaging target site of the subject, generates electric charges, and creates image information representing a radiographic image on the basis of the generated electric charge quantity. The cradle 130 charges a battery that is built into the electronic cassette 40. The console 110 controls the electronic cassette 40 and the radiation generator 120.

The console 110 acquires various types of information (data) stored in the database 150A from the RIS server 150, stores the data in a later-described HDD 116 (see FIG. 8), uses the data as needed to control the electronic cassette 40 and the radiation generator 120.

Figure 2:
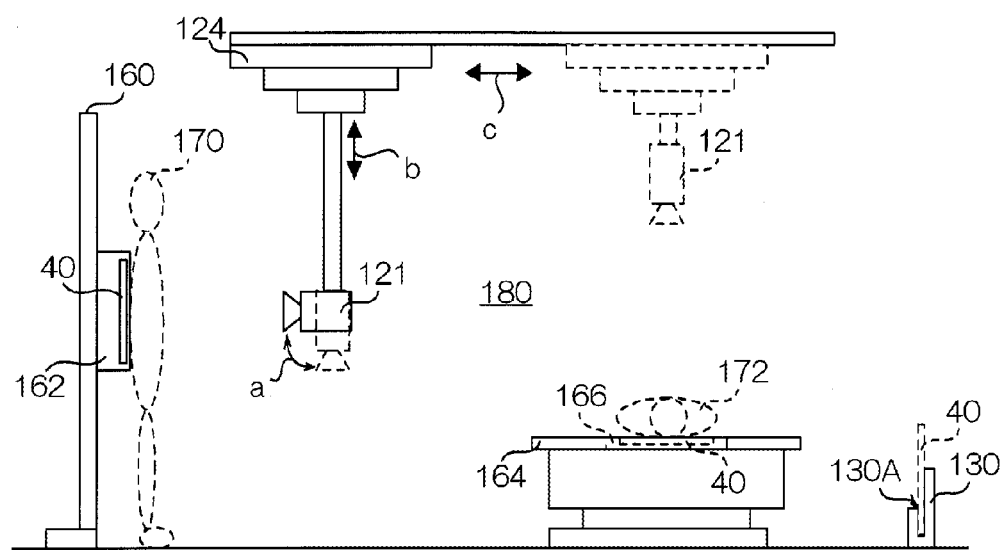
FIG. 2 is a side view illustrating an example arrangement of each device in a radiographic imaging room of the radiographic image capture system.

FIG. 2 shows an example arrangement of the devices, in a radiographic imaging room 180, of the imaging system 104 pertaining to the present exemplary embodiment.

As shown in FIG. 2, a standing position stand 160, which is used in cases of performing radiographic imaging in a standing position, and a lying position table 164, which is used in cases of performing radiographic imaging in a lying position, are installed in the radiographic imaging room 180. The space in front of the standing position stand 160 serves as a subject imaging position 170 when performing radiographic imaging in the standing position. The space above the lying position table 164 serves as a subject imaging position 172 when performing radiographic imaging in the lying position.

A holding unit 162 that holds the electronic cassette 40 is disposed in the standing position stand 160. The electronic cassette 40 is held at the holding unit 162 when capturing a radiographic image in the standing position. Similarly, a holding unit 166 that holds the electronic cassette 40 is disposed in the lying position table 164. The electronic cassette 40 is held at the holding unit 166 when capturing a radiographic image in the lying position.

Further, a supporting and moving mechanism 124 is disposed in the radiographic imaging room 180. In order to enable both radiographic imaging in the standing position and in the lying position by the radiation from the single radiation source 121, the supporting and moving mechanism 124 supports the radiation source 121 in such a way that the radiation source 121 is rotatable about a horizontal axis (the direction of arrow a in FIG. 2), is movable in the vertical direction (the direction of arrow b in FIG. 2), and is movable in the horizontal direction (the direction of arrow c in FIG. 2). The supporting and moving mechanism 124 includes a drive source that rotates the radiation source 121 about the horizontal axis, a drive source that moves the radiation source 121 in the vertical direction, and a drive source that moves the radiation source 121 in the horizontal direction (illustration of the drive sources are omitted in the drawings).

An accommodating portion 130A that can accommodate the electronic cassette 40 is formed in the cradle 130.

When the electronic cassette 40 is not in use, the electronic cassette 40 is accommodated in the accommodating portion 130A of the cradle 130, and the built-in battery of the electronic cassette 40 is charged by the cradle 130. When a radiographic image is to be captured, the electronic cassette 40 is removed from the cradle 130 by, for example, a radiologic technologist and is held in the holding unit 162 of the standing position stand 160 if the imaging posture is the standing position or is held in the holding unit 166 of the lying position table 164 if the imaging posture is the lying position.

In the imaging system 104 pertaining to the present exemplary embodiment, various types of information (data) are transmitted and received by wireless communication between the radiation generator 120 and the console 110 and between the electronic cassette 40 and the console 110.

The electronic cassette 40 is not limited to only being employed in a state held by the holding unit 162 of the standing position stand 160 or the holding unit 166 of the lying position table 164. Due to its portability, the electronic cassette 40 may also be employed unrestrained by a holding unit, for example when imaging arm or leg regions of a subject.

Figure 3:
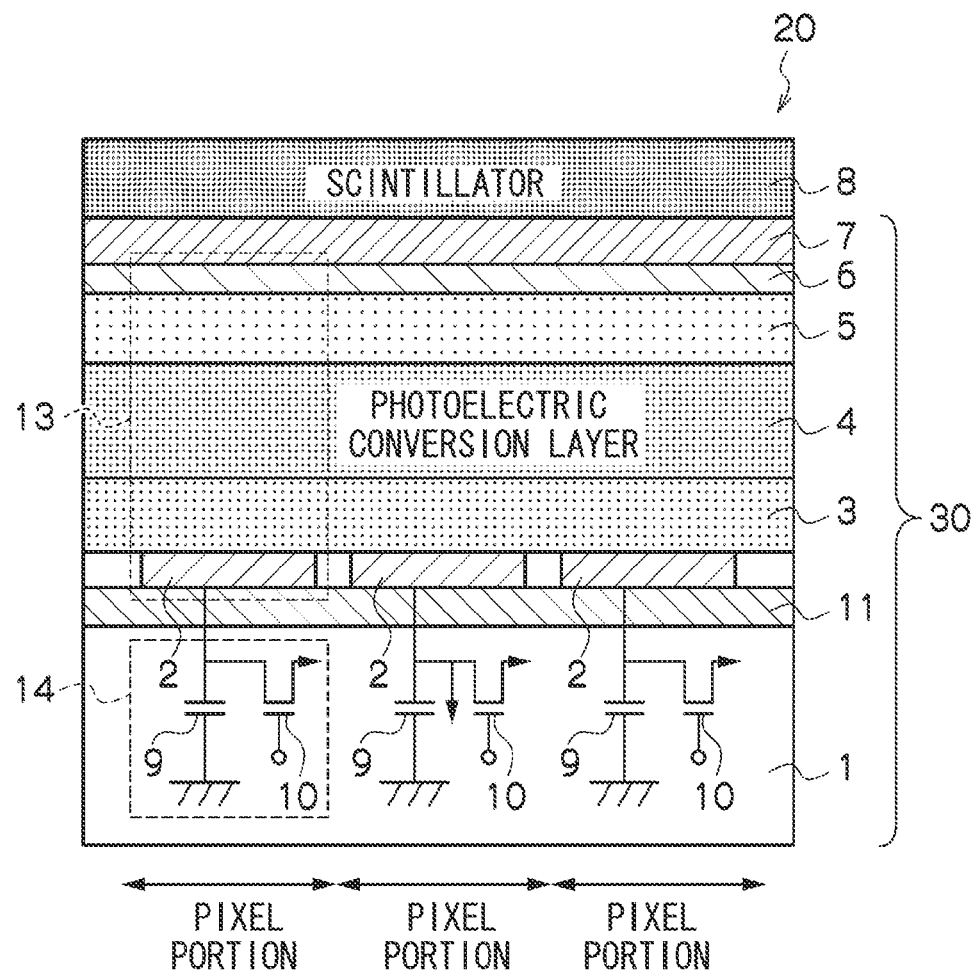
FIG. 3 is a cross-sectional diagram illustrating a schematic configuration of a portion including three pixels of a radiation detector of an exemplary embodiment.

Next, the configuration of the radiation detector 20 pertaining to the present exemplary embodiment will be described. FIG. 3 is a cross-sectional diagram schematically showing a portion including three pixels of the radiation detector 20 pertaining to the present exemplary embodiment.

As shown in FIG. 3, in the radiation detector 20 pertaining to the present exemplary embodiment, signal output portions 14, sensor portions 13, and a scintillator 8 are sequentially layered on an insulating substrate 1. Pixels are configured by the signal output portions 14 and the sensor portions 13. The pixels are arrayed on the substrate 1 and are configured in such a way that the signal output portion 14 and the sensor portion 13 in each pixel have overlap.

The scintillator 8 is formed on the sensor portions 13 with a transparent insulating film 7 being interposed therebetween. The scintillator 8 is formed of a phosphor material that converts radiation made incident thereon from above (the opposite side of the substrate 1) or below into light and emits light. By disposing the scintillator 8, the radiation that has passed through the subject is absorbed by the scintillator 8 and light is emitted.

It is preferred that the wavelength range of the light emitted by the scintillator 8 be in the visible light range (a wavelength of 360 nm to 830 nm). It is more preferred that the wavelength range of the light that the scintillator 8 emits include the green wavelength range in order to enable monochrome imaging by the radiation detector 20.

As the phosphor used for the scintillator 8, specifically a phosphor including cesium iodide (CsI) is preferred in the case of imaging using X-rays as the radiation. Using CsI(Tl) (cesium iodide to which thallium has been added) whose emission spectrum when X-rays are applied is 400 nm to 700 nm is particularly preferred. The emission peak wavelength in the visible light range of CsI(Tl) is 565 nm.

The sensor portions 13 have an upper electrode 6, lower electrodes 2, and a photoelectric conversion layer 4 that is placed between the upper electrode 6 and the lower electrodes 2. The photoelectric conversion layer 4 is configured by an organic photoelectric conversion material that absorbs the light emitted by the scintillator 8 and generates electric charge.

It is preferred that the upper electrode 6 be configured by a conducting material that is transparent at least with respect to the emission wavelength of the scintillator 8 because it is necessary to allow the light produced by the scintillator 8 to be made incident on the photoelectric conversion layer 4. Specifically, using a transparent conducting oxide (TCO) whose transmittance with respect to visible light is high and whose resistance value is small is preferred. A metal thin film of Au or the like may also be used as the upper electrode 6, but its resistance value easily increases when trying to obtain a transmittance of 90% or more, so TCO is more preferred. For example, ITO, IZO, AZO, FTO, $SnO_2$, $TiO_2$, $ZnO_2$, etc. may be preferably used. ITO is most preferred from the standpoints of process ease, low resistance, and transparency. The upper electrode 6 may have a single configuration common to all the pixels or may be divided per pixel.

The photoelectric conversion layer 4 includes an organic photoelectric conversion material, absorbs the light emitted from the scintillator 8, and generates an electric charge corresponding to the absorbed light. The photoelectric conversion layer 4 including the organic photoelectric conversion material in this way has a sharp absorption spectrum in the visible range, virtually no electromagnetic waves other than the light emitted by the scintillator 8 are absorbed by the photoelectric conversion layer 4, and noise that is generated as a result of radiation such as X-rays is effectively prevented from being absorbed by the photoelectric conversion layer 4.

It is preferred that the absorption peak wavelength of the organic photoelectric conversion material configuring the photoelectric conversion layer 4 be as close as possible to the emission peak wavelength of the scintillator 8 so that the organic photoelectric conversion material most efficiently absorbs the light emitted by the scintillator 8. It is ideal that the absorption peak wavelength of the organic photoelectric conversion material and the emission peak wavelength of the scintillator 8 coincide, but as long as the difference between them is small, the organic photoelectric conversion material can sufficiently absorb the light emitted from the scintillator 8. Specifically, it is preferred that the difference between the absorption peak wavelength of the organic photoelectric conversion material and the emission peak wavelength of the scintillator 8 with respect to radiation be within 10 nm. It is more preferred that the difference be within 5 nm.

Examples of organic photoelectric conversion materials that can satisfy this condition include quinacridone organic compounds and phthalocyanine organic compounds. For example, the absorption peak wavelength in the visible range of quinacridone is 560 nm. Therefore, if quinacridone is used as the organic photoelectric conversion material and CsI(Tl) is used as the material of the scintillator 8, it is possible to make the difference between the peak wavelengths within 5 nm, and the amount of electric charge generated in the photoelectric conversion layer 4 may be substantially maximized.

Next, the photoelectric conversion layer 4 applicable to the radiation detector 20 pertaining to the present exemplary embodiment will be specifically described.

An electromagnetic wave absorption/photoelectric conversion portion in the radiation detector 20 pertaining to the present exemplary embodiment may be configured by the pair of electrodes 2 and 6 and an organic layer that includes the photoelectric conversion layer 4 sandwiched between the electrodes 2 and 6. More specifically, the organic layer may be formed by stacking or mixing together a material that absorbs electromagnetic waves, a photoelectric conversion material, an electron-transporting material, a hole-transporting material, an electron-blocking material, a hole-blocking material, a crystallization preventing material, electrodes, an interlayer contact improving material, etc.

It is preferred that the organic layer contains an organic p-type compound or an organic n-type compound.

Organic p-type semiconductors (compounds) are donor organic semiconductors (compounds) represented mainly by hole-transporting organic compounds and refer to organic compounds having the property that they easily donate electrons. More specifically, organic p-type semiconductors (compounds) refer to organic compounds whose ionization potential is the smaller of the two when two organic materials are brought into contact with each other and used. Consequently, any organic compound may be used as the donor organic compound provided that it is an electron-donating organic compound.

Organic n-type semiconductors (compounds) are accepter organic semiconductors (compounds) represented mainly by electron-transporting organic compounds and refer to organic compounds having the property that they easily accept electrons. More specifically, organic n-type semiconductors (compounds) refer to organic compounds whose electron affinity is the greater of the two when two organic compounds are brought into contact with each other and used. Consequently, any organic compound may be used as the accepter organic compound provided that it is an electron-accepting organic compound.

Materials applicable as the organic p-type semiconductor and the organic n-type semiconductor, and the structure of the photoelectric conversion layer 4, are described in detail in JP-A No. 2009-32854, so descriptions thereof will be omitted here. The photoelectric conversion layer 4 may also be formed so as to further contain fullerenes or carbon nanotubes.

It is preferred that the thickness of the photoelectric conversion layer 4 be as large as possible in terms of absorbing the light from the scintillator 8. However, if the thickness of the photoelectric conversion layer 4 is thicker than a certain extent, the strength of the electric field generated in the photoelectric conversion layer 4 due to a bias voltage applied from both ends of the photoelectric conversion layer 4 drops and the electric charge become unable to be collected. For this reason, it is preferred that the thickness of the photoelectric conversion layer 4 be from 30 nm to 300 nm. It is more preferred that the thickness of the photoelectric conversion layer 4 be from 50 nm to 250 nm. It is particularly preferred that the thickness of the photoelectric conversion layer 4 be from 80 nm to 200 nm.

In the radiation detector 20 shown in FIG. 3, the photoelectric conversion layer 4 has a single configuration common to all the pixels, but the photoelectric conversion layer 4 may also be divided per pixel.

The lower electrodes 2 are thin films divided per pixel. The lower electrodes 2 may be configured by a transparent or opaque conducting material, and aluminum, silver, etc. may be suitably used.

The thickness of the lower electrodes 2 may be 30 nm to 300 nm, for example.

In the sensor portions 13, one of the electric charge (holes or electrons) generated in the photoelectric conversion layer 4 can be moved to the upper electrode 6 and the other can be moved to the lower electrodes 2 as a result of a predetermined bias voltage being applied between the upper electrode 6 and the lower electrodes 2. In the radiation detector 20, a wire is connected to the upper electrode 6, and the bias voltage is applied to the upper electrode 6 via this wire. The polarity of the bias voltage is decided in such a way that the electrons generated in the photoelectric conversion layer 4 move to the upper electrode 6 and the holes move to the lower electrodes 2, but embodiments are not limited to this configuration and the polarity may be the opposite.

It suffices for the sensor portions 13 configuring each of the pixels to include at least the lower electrodes 2, the photoelectric conversion layer 4, and the upper electrode 6. However, in order to prevent an increase in dark current, disposing at least either of an electron-blocking film 3 or a hole-blocking film 5 is preferred, and disposing both is more preferred.

The electron-blocking film 3 may be disposed between the lower electrodes 2 and the photoelectric conversion layer 4. The electron-blocking film 3 may prevent electrons from being injected from the lower electrodes 2 into the photoelectric conversion layer 4 and dark current from increasing when the bias voltage has been applied between the lower electrodes 2 and the upper electrode 6.

Electron-donating organic materials may be used for the electron-blocking film 3.

It suffices for the material that is actually used for the electron-blocking film 3 to be selected in accordance with, for example, the material of the adjacent electrodes and the material of the adjacent photoelectric conversion layer 4. A material whose electron affinity (Ea) is greater by 1.3 eV or more than the work function (Wf) of the material of the adjacent electrodes and has an ionization potential (Ip) equal to or smaller than the ionization potential of the material of the adjacent photoelectric conversion layer 4 is preferred. Materials applicable as the electron-donating organic material are described in detail in JP-A No. 2009-32854, so descriptions thereof will be omitted here.

In order to allow the electron-blocking film 3 to reliably exhibit a dark current preventing effect and to prevent a drop in the photoelectric conversion efficiency of the sensor portions 13, it is preferred that the thickness of the electron-blocking film 3 be from 10 nm to 200 nm. It is more preferred that the thickness of the electron-blocking film 3 be from 30 nm to 150 nm, and particularly preferred that the thickness of the electron-blocking film 3 be from 50 nm to 100 nm.

The hole-blocking film 5 may be disposed between the photoelectric conversion layer 4 and the upper electrode 6. The hole-blocking film 5 may prevent holes from being injected from the upper electrode 6 into the photoelectric conversion layer 4 and dark current from increasing when a bias voltage has been applied between the lower electrodes 2 and the upper electrode 6.

Electron-accepting organic materials may be used for the hole-blocking film 5.

In order to allow the hole-blocking film 5 to reliably exhibit a dark current preventing effect and to prevent a drop in the photoelectric conversion efficiency of the sensor portions 13, it is preferred that the thickness of hole-blocking film 5 be from 10 nm to 200 nm. It is more preferred that the thickness of the hole-blocking film 5 be from 30 nm to 150 nm, and particularly preferred that the thickness of the hole-blocking film 5 be from 50 nm to 100 nm.

It suffices for the material that is actually used for the hole-blocking film 5 to be selected in accordance with, for example, the material of the adjacent electrode and the material of the adjacent photoelectric conversion layer 4. A material whose ionization potential (Ip) is greater by 1.3 eV or more than the work function (Wf) of the material of the adjacent electrode and has an electron affinity (Ea) equal to or greater than the electron affinity of the material of the adjacent photoelectric conversion layer 4 is preferred. Materials applicable as the electron-accepting organic material are described in detail in JP-A No. 2009-32854, so descriptions thereof will be omitted here.

In a case in which the bias voltage is set in such a way that, among the electric charge generated in the photoelectric conversion layer 4, the holes move to the upper electrode 6 and the electrons move to the lower electrode 2, the positions of the electron-blocking film 3 and the hole-blocking film 5 may be reversed. Further, the electron-blocking film 3 and the hole-blocking film 5 do not both have to be disposed; a certain degree of a dark current preventing effect may be obtained as long as either is disposed.

Figure 4:
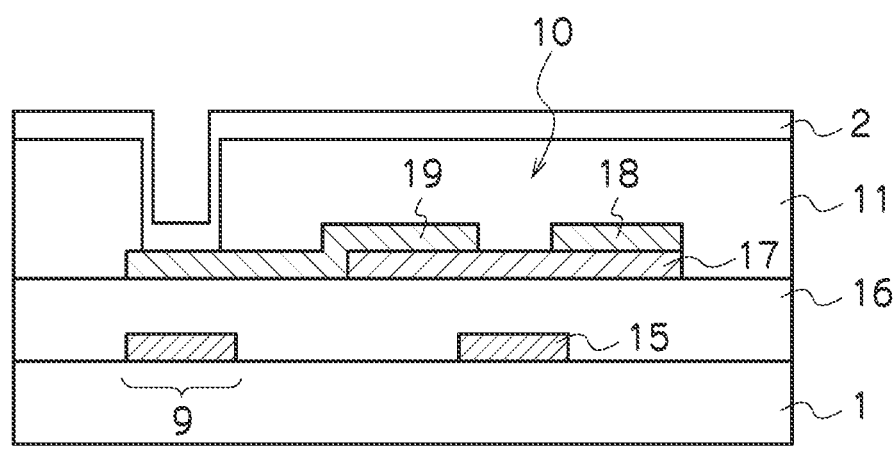
FIG. 4 a cross-sectional side view schematically illustrating the configuration of a signal output portion for a single pixel of the radiation detector.

The signal output portions 14 are formed on the surface of the substrate 1 below the lower electrodes 2 of each of the pixels. FIG. 4 schematically shows the configuration of one of the signal output portions 14.

As shown in FIG. 4, in each of the signal output portions 14, a capacitor 9 and a field-effect thin-film transistor (TFT) (hereinafter sometimes this will be simply called a "thin-film transistor") 10 are formed in correspondence to the lower electrode 2. The capacitor 9 stores the electric charge that has moved to the lower electrode 2. The thin-film transistor 10 converts the electric charge stored in the capacitor 9 into an electric signal and outputs the electric signal. The region in which the capacitor 9 and the thin-film transistor 10 are formed has a portion that overlaps the lower electrode 2 in a plan view. Due to this configuration, the signal output portion 14 and the sensor portion 13 in each of the pixels have an overlap in the thickness direction. In order to minimize the plane area of the radiation detector 20 (the pixels), it is preferred that the region in which the capacitor 9 and the thin-film transistor 10 are formed be completely covered by the lower electrode 2.

The capacitor 9 is electrically connected to the corresponding lower electrode 2 via a wire of a conductive material that is formed penetrating an insulating film 11 disposed between the substrate 1 and the lower electrode 2. Because of this, the electric charge trapped in the lower electrode 2 can be moved to the capacitor 9.

A gate electrode 15, a gate insulating film 16, and an active layer (channel layer) 17 are layered in the thin-film transistor 10. A source electrode 18 and a drain electrode 19 are formed a predetermined spacing apart from each other on the active layer 17.

The active layer 17 may, for example, be formed by amorphous silicon, an amorphous oxide, an organic semiconductor material, carbon nanotubes, etc. The material configuring the active layer 17 is not limited to these.

In a case in which the active layer 17 is configured by an amorphous oxide, oxides including at least one of In, Ga, and Zn (e.g., In—O amorphous oxides) are preferred, oxides including at least two of In, Ga, and Zn (e.g., In—Zn—O amorphous oxides, In—Ga—O amorphous oxides, or Ga—Zn—O amorphous oxides) are more preferred, and oxides including In, Ga, and Zn are particularly preferred. As an In—Ga—Zn—O amorphous oxide, an amorphous oxide whose composition in a crystalline state is expressed by $InGaO_3(ZnO)_m$, (where m is a natural number less than 6) is preferred, and particularly $InGaZnO_4$ is preferred.

Examples of organic semiconductor materials capable of configuring the active layer 17 include phthalocyanine compounds, pentacene, and vanadyl phthalocyanine, but the organic semiconductor materials are not limited to these. Configurations of phthalocyanine compounds are described in detail in JP-A No. 2009-212389, so descriptions thereof will be omitted here.

By forming the active layer 17 of the thin-film transistor 10 from an amorphous oxide, an organic semiconductor material, or carbon nanotubes, the active layer 17 does not absorb radiation such as X-rays, or if it does absorb any radiation the radiation is an extremely minute amount, so the generation of noise in the signal output portion 14 may be effectively prevented.

Further, in a case in which the active layer 17 is formed with carbon nanotubes, the switching speed of the thin-film transistor 10 may be increased, and the thin-film transistor 10 may be formed having a low degree of absorption of light in the visible light range. In the case of forming the active layer 17 with carbon nanotubes, the performance of the thin-film transistor 10 drops significantly even if an infinitesimal amount of a metal impurity is mixed into the active layer 17, so it is necessary to separate, extract, and form extremely high-purity carbon nanotubes using centrifugal separation or the like.

Here, the amorphous oxide, organic semiconductor material, or carbon nanotubes configuring the active layer 17 of the thin-film transistor 10 and the organic photoelectric conversion material configuring the photoelectric conversion layer 4 are all capable of being formed into films at a low temperature. Consequently, the substrate 1 is not limited to a substrate with high heat resistance, such as a semiconductor substrate, a quartz substrate, or a glass substrate, and a plastic or other flexible substrate, aramids, or bionanofibers may also be used. Specifically, polyester, such as polyethylene terephthalate, polybutylene phthalate, and polyethylene naphthalate, polystyrene, polycarbonate, polyethersulphone, polyarylate, polyimide, polycyclic olefin, norbornene resin, and poly(chloro-trifluoro-ethylene) or other flexible substrates may be used. By employing a flexible substrate made of plastic, the substrate may be made lightweight, which is advantageous for portability.

Further, an insulating layer for ensuring insulation, a gas barrier layer for preventing the transmission of at least one of moisture or oxygen, an undercoat layer for improving flatness or adhesion to the electrodes or the like, or other layers may also be disposed on the substrate 1.

High-temperature processes of 200 degrees or higher can be applied to aramids, so a transparent electrode material can be hardened at a high temperature and given a low resistance, and aramids can also accommodate automatic packaging of driver ICs including solder reflow processes. Aramids also have a thermal expansion coefficient that is close to that of indium tin oxide (ITO) or a glass substrate, so they have little warping after manufacture and do not break easily. Further, it is possible to form a thinner substrate with aramids compared to a glass substrate or the like. An ultrathin glass substrate and an aramid may also be layered to form a substrate.

Further, bionanofibers are composites of cellulose microfibril bundles (bacterial cellulose) that a bacterium (*Acetobacter xylinum*) produces and a transparent resin. Cellulose microfibril bundles have a width of 50 nm, which is a size that is 1/10 with respect to visible wavelengths, and have high strength, high elasticity, and low thermal expansion. By impregnating and hardening a transparent resin such as an acrylic resin or an epoxy resin in bacterial cellulose, it is possible to obtain bionanofibers exhibiting a light transmittance of about 90% at a wavelength of 500 nm while including fibers at 60 to 70%. Bionanofibers have a low thermal expansion coefficient (3 to 7 ppm) comparable to silicon crystal, a strength comparable to steel (460 MPa), high elasticity (30 GPa), and are flexible, so they enables to form the substrate 1 thinner compared to a glass substrate or the like.

In the present exemplary embodiment, a TFT substrate 30 is formed by sequentially forming the signal output portions 14, the sensor portions 13, and the transparent insulating film 7 on the substrate 1, and the radiation detector 20 is formed by adhering the scintillator 8 onto the TFT substrate 30 using, for example, an adhesive resin whose light absorbance is low.

Figure 5:
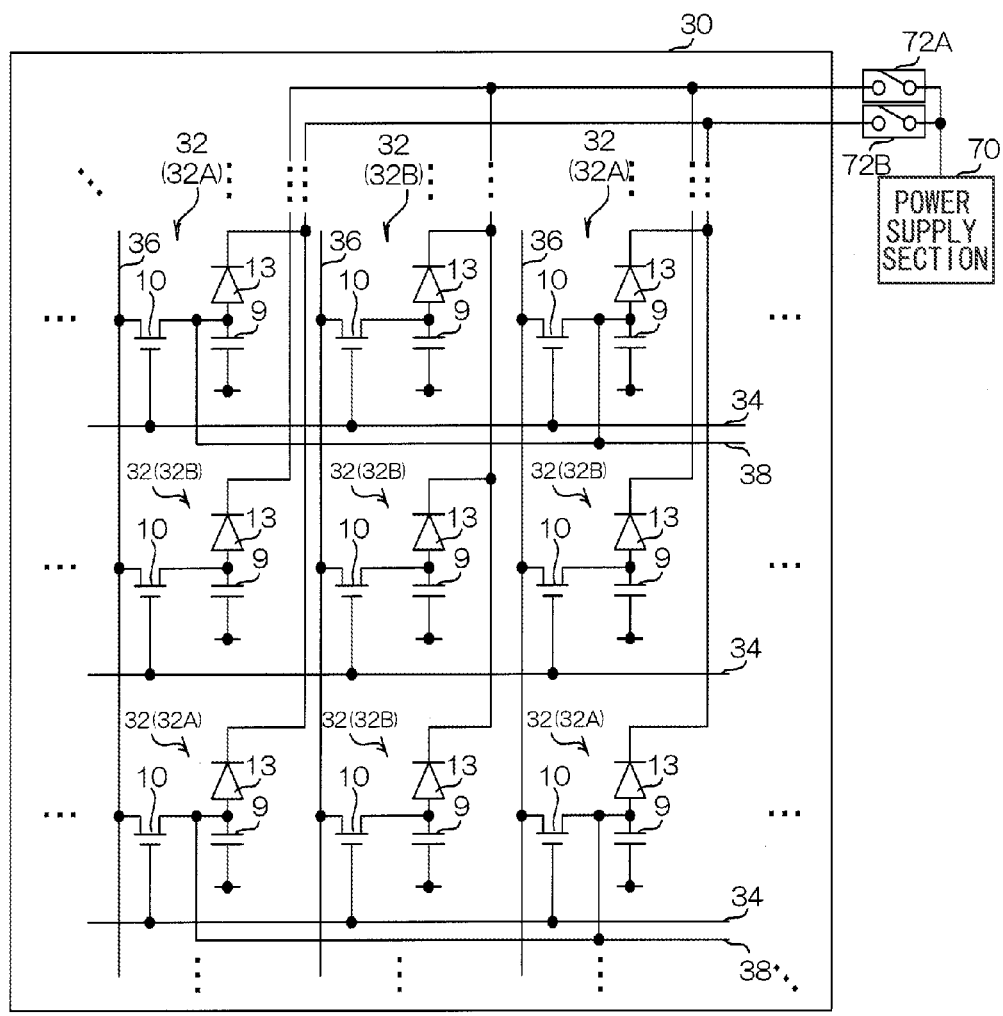
FIG. 5 is a plan view illustrating the configuration of the radiation detector.

As shown in FIG. 5, on the TFT substrate 30, pixels 32 including the sensor portions 13, the capacitors 9, and the thin-film transistors 10 are plurally disposed two-dimensionally in one direction (a direction along gate lines 34 in FIG. 5) and an intersecting direction (a direction along data lines 36 in FIG. 5) with respect to the one direction.

Further, plural gate lines 34 that extends in the one direction and are for switching on and off the thin-film transistors 10 and plural data lines 36 that extends in the intersecting direction and are for reading out the electric charges via the thin-film transistors 10 in an on-state are disposed in the radiation detector 20.

The radiation detector 20 is formed in a tabular, quadrilateral shape having four sides on its outer edges in a plan view; more specifically, the radiation detector 20 is formed in a rectangular shape.

In the radiation detector 20 pertaining to the present exemplary embodiment, some of the pixels 32 are used for detecting the state of application of the radiation, and the remaining pixels 32 capture radiographic images. Hereinafter, the pixels 32 for detecting the state of application of the radiation will be called radiation detection pixels (detection pixels) 32A, and the remaining pixels 32 will be called radiographic imaging acquiring pixels (imaging pixels) 32B.

The radiation detector 20 pertaining to the present exemplary embodiment cannot obtain pixel information (data) of radiographic images in the positions where the detection pixels 32A are placed because the radiation detector 20 captures radiographic images with the imaging pixels 32B excluding the detection pixels 32A of the pixels 32. For this reason, in the radiation detector 20, the detection pixels 32A are placed in such a way as to be dispersed and the console 110 executes missing pixel correction that generates pixel data of radiographic images in the positions where the detection pixels 32A are placed by interpolation using pixel data that has been obtained by the imaging pixels 32B positioned around those detection pixels 32A.

In order to detect radiation application states a radiation application amount acquisition function is provided to the electronic cassette 40 of the present exemplary embodiment. The radiation application amount acquisition function acquires data expressing the application amount of radiation X from the radiation source 121 (referred to below as radiation application amount data).

Therefore, in the radiation detector 20, as shown in FIG. 5, direct read-out lines 38, to which connecting portions between the capacitors 9 and the thin-film transistors 10 in the detection pixels 32A are connected and which are for directly reading out the electric charges stored in those capacitors 9, are disposed extending in the gate-line direction. In the radiation detector 20 pertaining to the present exemplary embodiment, one direct read-out line 38 is allocated with respect to plural detection pixels 32A arranged side by side in the gate-line direction, and the connecting portions between the capacitors 9 and the thin-film transistors 10 in those plural detection pixels 32A are connected to a common (single) direct read-out line 38.

The sensor portion 13 of each of the detection pixels 32A is connected to one terminal of a switch 72B through a common signal line, and the sensor portion 13 of each of the imaging pixels 32B is connected to one terminal of a switch 72A through a common signal line. The other respective terminals of the switch 72A and the switch 72B are connected to a power supply section 70, described later, (see FIG. 8). The switch 72A and the switch 72B enable separate control of at least one of application/non-application of a bias voltage to the sensor portion 13 of each of the detection pixels 32A, or application/non-application of a bias voltage to the sensor portion 13 of each of the imaging pixels 32B.

In the electronic cassette 40 of the present exemplary embodiment, the switch 72A and the switch 72B are provided as separate components from the radiation detector 20. However, embodiments are not limited thereto and the switch 72A and the switch 72B may be integrally provided with the radiation detector 20.

Figure 6:
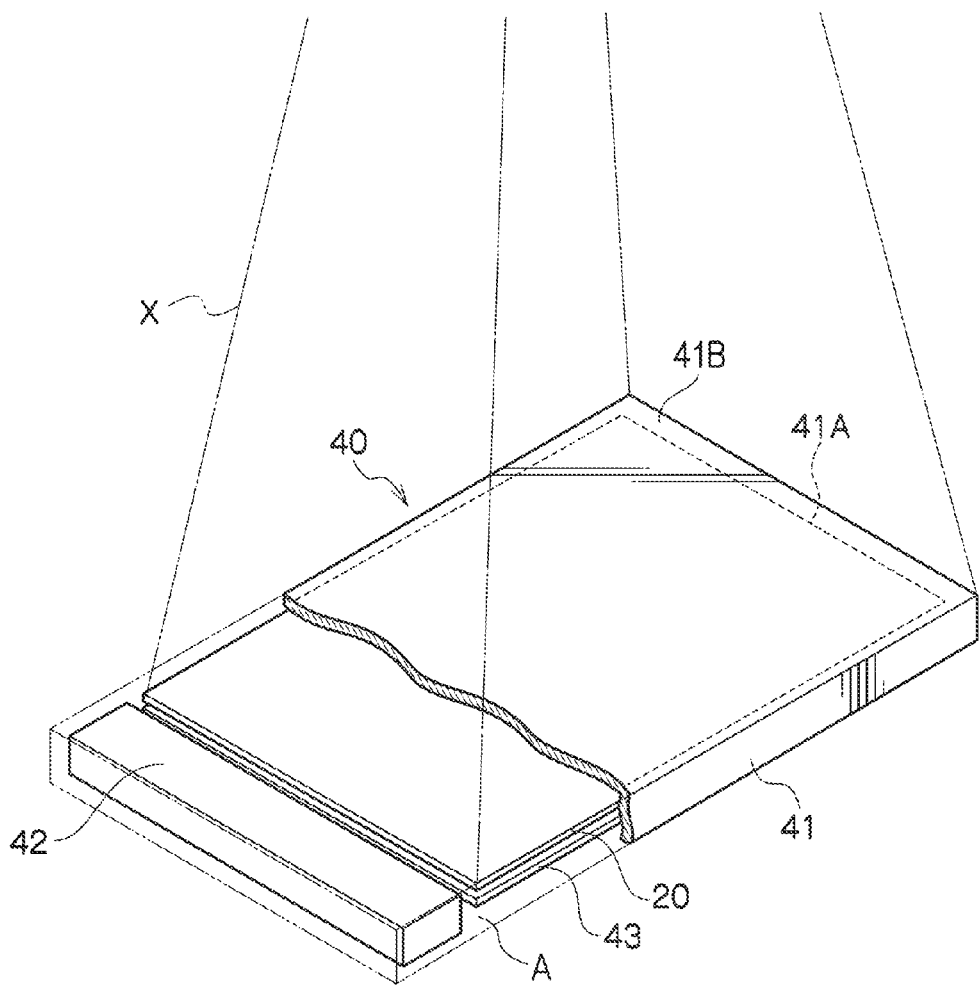
FIG. 6 is a perspective view illustrating the configuration of an electronic cassette.

Next, the configuration of the electronic cassette 40 pertaining to the present exemplary embodiment will be described. FIG. 6 is a perspective view showing the configuration of the electronic cassette 40.

As shown in FIG. 6, the electronic cassette 40 is equipped with a housing 41 that is formed from a material that allows radiation to pass through, and the electronic cassette 40 is given a waterproof and airtight structure. When the electronic cassette 40 is used in an operating room or the like, there is the concern that blood or other contaminants may adhere to the electronic cassette 40. Therefore, by giving the electronic cassette 40 a waterproof and airtight structure and disinfecting the electronic cassette 40 as needed, the single electronic cassette 40 may be used repeatedly.

A space A that accommodates various parts is formed inside the housing 41. The radiation detector 20, which detects the radiation X that has passed through the subject, and a lead plate 43, which absorbs backscattered rays of the radiation X, are disposed in this order inside the space A from a side of the housing 41 to which the radiation X is applied.

In the electronic cassette 40, the region corresponding to the disposed position of the radiation detector 20 in one surface of the tabular shape of the housing 41 is configured as a quadrilateral imaging region 41A that is capable of detecting radiation. The surface having the imaging region 41A of the housing 41 is configured as a top plate 41B of the electronic cassette 40. In the electronic cassette 40, the radiation detector 20 is placed in such a way that the TFT substrate 30 is at the top plate 41B side, and the radiation detector 20 is adhered to the inner surface of the top plate 41B (the back surface of the top plate 41B at the opposite side of the surface on which the radiation is made incident) in the housing 41.

As shown in FIG. 6, a case 42 that accommodates a cassette controller 58 and the power supply section 70 (see FIG. 8 for both) is placed at one end side of the interior of the housing 41 in a position that does not overlap with the radiation detector 20 (outside the range of the imaging region 41A).

The case 41 is configured by carbon fiber, aluminum, magnesium, bionanofibers (cellulose microfibrils), or a composite material, for example, in order to make the entire electronic cassette 40 lightweight.

As the composite material, for example, a material including reinforced fiber resin is used, and carbon, cellulose, or the like is included in the reinforced fiber resin. Specifically, as the composite material, carbon fiber reinforced plastic (CFRP), a composite material with a structure where a foam material is sandwiched by CFRP, or a composite material in which the surface of a foam material is coated with CFRP may be used. In the present exemplary embodiment, a composite material with a structure where a foam material is sandwiched by CFRP is used. Thereby, the strength (rigidity) of the housing 41 may be raised compared to a case in which the housing 41 is configured by a carbon alone.

Figure 7:
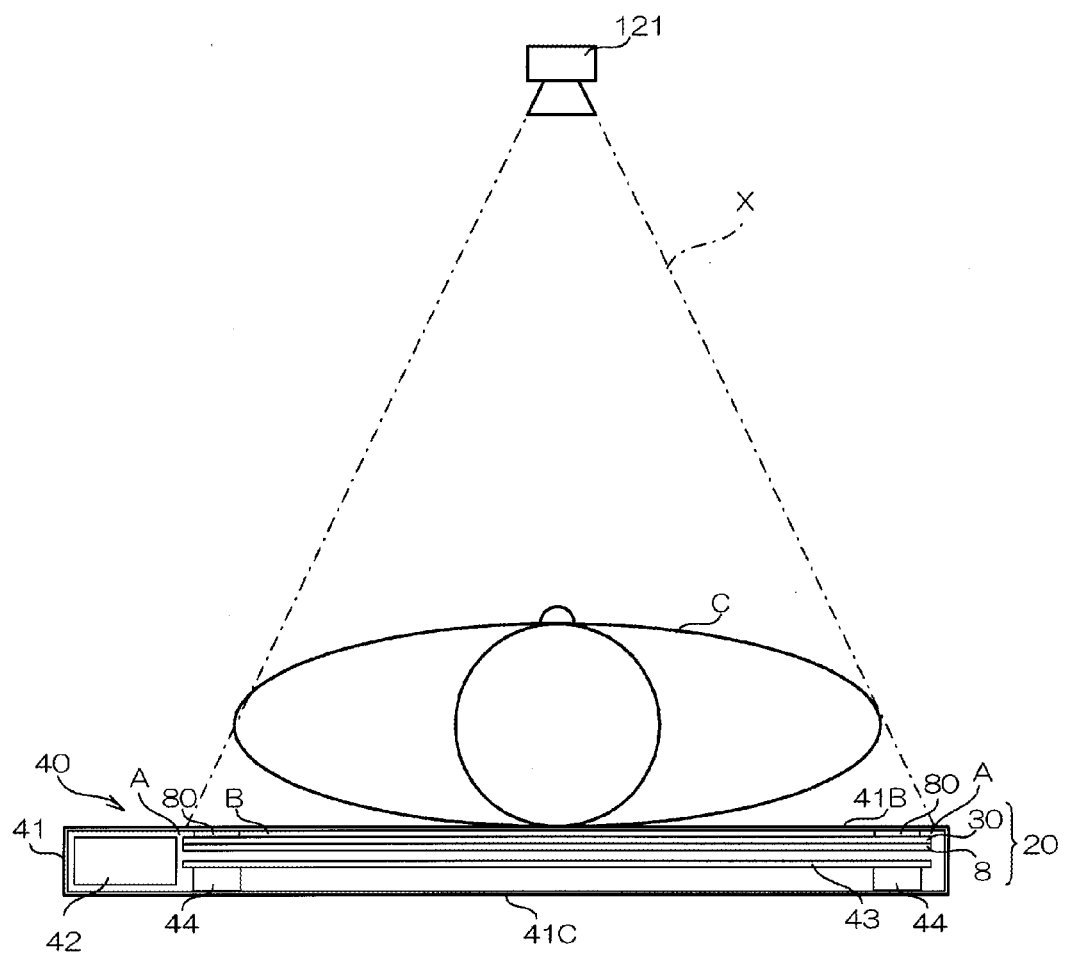
FIG. 7 is a cross-sectional side view illustrating the electronic cassette.

As shown in FIG. 7, inside the housing 41, support members 44 are disposed on the inner surface of a back surface 41C opposing the top plate 41B. The radiation detector 20 and the lead plate 43 are placed in this order in the application direction of the radiation X between the support members 44 and the top plate 41B. The support members 44 are configured by a foam material, for example, from the standpoint of reducing weight and absorbing dimensional deviations, and the support members 44 support the lead plate 43.

As shown in FIG. 7, adhesive members 80 that detachably adhere the TFT substrate 30 of the radiation detector 20 are disposed at the inner surface of the top plate 41B. Double-sided tape, for example, may be used as the adhesive members 80. In this case, the double-sided tape is formed in such a way that the adhesive force of one adhesive surface is stronger than that of the other adhesive surface.

Specifically, the surface having a weak adhesive force (weak adhesive surface) is set to have a 180-degree peel strength equal to or less than 1.0 N/cm. The surface having a strong adhesive force (strong adhesive surface) contacts the top plate 41B, and the weak adhesive surface contacts the TFT substrate 30. Because of this configuration, the thickness of the electronic cassette 40 may be made thin compared to a case in which the radiation detector 20 is fixed to the top plate 41B by, for example, fixing members such as screws. Further, even if the top plate 41B deforms due to a shock or a load, the radiation detector 20 follows the deformation of the top plate 41B which has high rigidity, so only deformation of large curvature (a gentle curve) arises and the potential for the radiation detector 20 to break due to localized deformation of low curvature will be low. Moreover, the radiation detector 20 contributes to improving the rigidity of the top plate 41B.

In this way, in the electronic cassette 40, since the radiation detector 20 is adhered to the inner surface of the top plate 41B of the housing 41, the housing 41 is separable into two between the top plate 41B side and the back surface 41C side, and the housing 41 may be separated into two of the top plate 41B side and the back surface 41C side when the radiation detector 20 is adhered to the top plate 41B or when the radiation detector 20 is detached from the top plate 41B.

In the present exemplary embodiment, the adhesion of the radiation detector 20 to the top plate 41B does not have to be performed in a clean room or the like. The reason is because, even if foreign materials such as metal fragments that absorb radiation have been incorporated between the radiation detector 20 and the top plate 41B, the foreign materials can be removed by detaching the radiation detector 20 from the top plate 41B.

Next, the configurations of relevant portions of an electrical system of the imaging system 104 pertaining to the present exemplary embodiment will be described with reference to FIG. 8.

Figure 8:
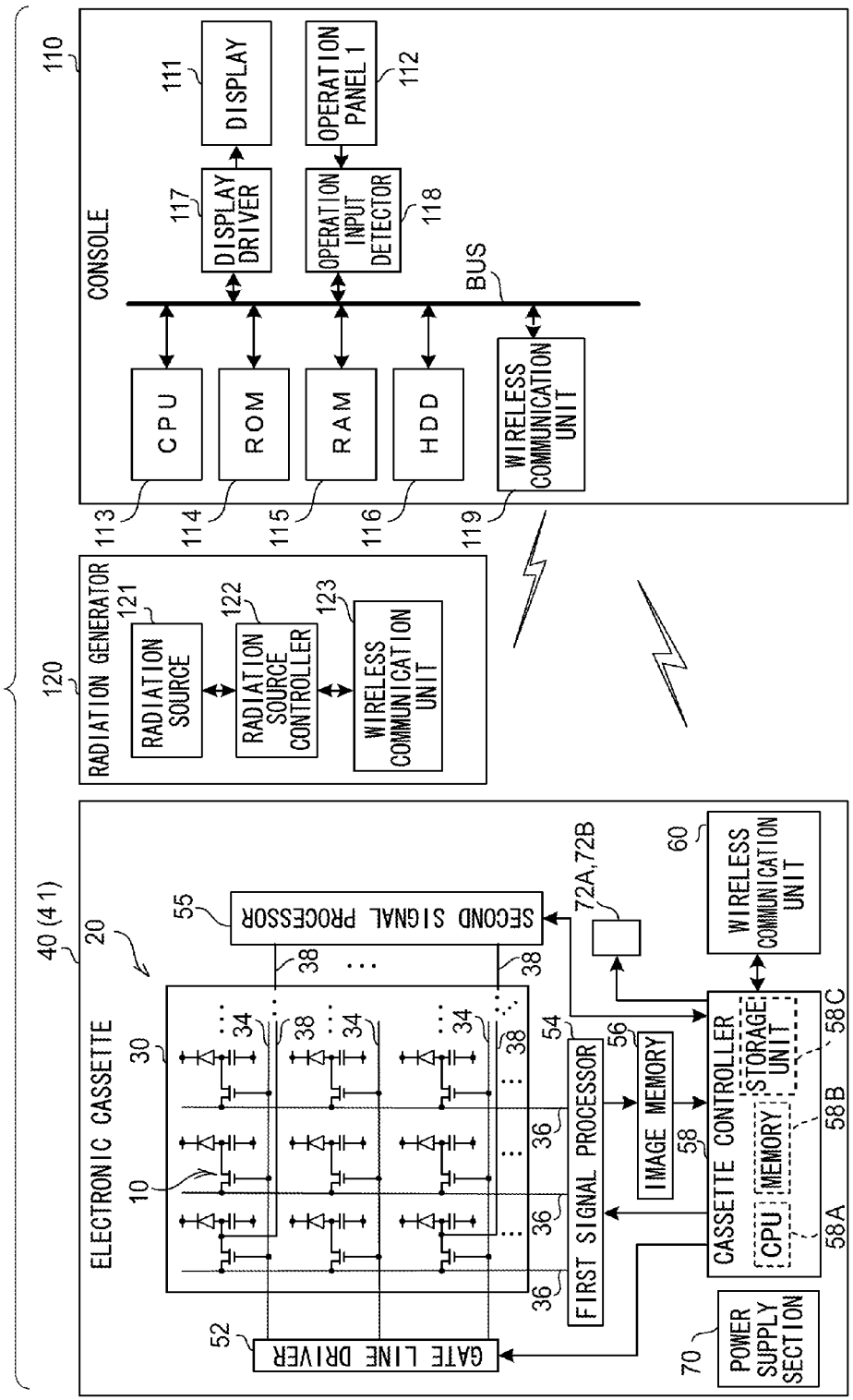
FIG. 8 is a block diagram illustrating relevant portions of an electrical system of the radiographic image capture system.

As shown in FIG. 8, in the radiation detector 20 built into the electronic cassette 40, a gate line driver 52 is placed on one side of two sides adjacent to each other, and a first signal processor 54 is placed on the other side. The individual gate lines 34 of the TFT substrate 30 are connected to the gate line driver 52, and the individual data lines 36 of the TFT substrate 30 are connected to the first signal processor 54.

An image memory 56, the cassette controller 58, and a wireless communication unit 60 are disposed inside the housing 41.

The thin-film transistors 10 of the TFT substrate 30 are sequentially switched on in row units by signals supplied via the gate lines 34 from the gate line driver 52, and the electric charges that have been read out by the thin-film transistors 10 switched to an on-state are transmitted through the data lines 36 as electric signals and are inputted to the first signal processor 54. Thus, the electric charges are sequentially read out in row units, and a two-dimensional radiographic image can be acquired.

While omitted from illustration, for every individual data line 36 the first signal processor 54 is equipped with an amplifier circuit, for amplifying input electrical signals, and a sample-and-hold circuit. Electrical signals transmitted by the individual data lines 36 are held in the sample-and-hold circuits after amplification by the amplifier circuits. A multiplexer and an analog-to-digital (A/D) converter are connected in sequence to the output side of the sample-and-hold circuits. The electrical signals held in the individual sample-and-hold circuits are input in sequence (serially) to the multiplexer and converted into digital image data by the A/D converter.

The image memory 56 is connected to the first signal processor 54. The image data outputted from the A/D converter of the first signal processor 54 are sequentially stored in the image memory 56. The image memory 56 has a storage capacity that is capable of storing image data for a predetermined number of frames' worth of radiographic images. Each time radiographic imaging is performed, the image data obtained by the imaging are sequentially stored in the image memory 56.

The image memory 56 is also connected to the cassette controller 58. The cassette controller 58 includes a microcomputer, which is equipped with a central processing unit (CPU) 58A, a memory 58B including a read-only memory (ROM) and a random access memory (RAM), and a non-volatile storage unit 58C including a flash memory or the like, and controls the operations of the entire electronic cassette 40.

Further, the wireless communication unit 60 is connected to the cassette controller 58. The wireless communication unit 60 is adapted to a wireless local area network (LAN) standard represented by IEEE (Institute of Electrical and Electronics Engineers) 802.11a/b/g/n or the like and controls the transmission of various types of information (data) between the electronic cassette 40 and external devices by wireless communication. Via the wireless communication unit 60, the cassette controller 58 is made capable of wireless communication with external devices such as the console 110 that performs control relating to radiographic imaging and is made capable of transmitting and receiving various types of data to and from the console 110 and the like.

In the radiation detector 20, a second signal processor 55 is placed on the opposite side of the gate line driver 52 across the TFT substrate 30 in order to realize the radiation application amount acquisition function mentioned above. The individual direct read-out lines 38 of the TFT substrate 30 are connected to the second signal processor 55.

The second signal processor 55 is equipped with an amplifier circuit and an A/D converter provided one for each of the direct read-out lines 38, and is connected to the cassette controller 58. The second signal processor 55, under control from the cassette controller 58, performs sampling of each of the direct read-out lines 38 at a specific cycle, converts the electrical signals transmitted by each of the direct read-out lines 38 into digital data and outputs the converted digital data in sequence to the cassette controller 58. The combined value of the digital data for each of the direct read-out lines 38 indicates the radiation application amount, and corresponds to the radiation application amount data referred to above.

Control terminals of the switch 72A and the switch 72B are connected to the cassette controller 58. The cassette controller 58 is accordingly capable of separately controlling the open or closed states of the switch 72A and the switch 72B.

Further, the power supply section 70 is disposed in the electronic cassette 40. The various circuits and elements described above (the gate line driver 54, the first signal processor 54, the second signal processor 55, the image memory 56, the wireless communication unit 60, the microcomputer functioning as the cassette controller 58, etc.) are actuated by power supplied from the power supply section 70. The power supply section 70 has a built-in battery (a rechargeable secondary battery) so as to not impair the portability of the electronic cassette 40, and the power supply section 70 supplies power to the various circuits and elements from the charged battery. In FIG. 8, illustration of wires connecting the various circuits and elements to the power supply section 70 is omitted.

As shown in FIG. 8, the console 110 is configured as a server computer and is equipped with a display 111, which displays operation menus, captured radiographic images, and so forth, and an operation panel 112, which is configured to include plural keys and by which various types of information (data) and operation instructions are inputted.

The console 110 is equipped with a CPU 113 that controls the operations of the entire device, a ROM 114 in which various programs including a control program are stored in advance, a RAM 115 that temporarily stores various types of data, a hard disk drive (HDD) 116 that stores and holds various types of data, a display driver 117 that controls the display of various types of information on the display 111, and an operation input detector 118 that detects states of operation with respect to the operation panel 112. Further, the console 110 is equipped with a wireless communication unit 119 that transmits and receives various types of information (data) such as later-described exposure conditions to and from the radiation generator 120 by wireless communication and also transmits and receives various types of information (data) such as image data to and from the electronic cassette 40 by wireless communication.

The CPU 113, the ROM 114, the RAM 115, the HDD 116, the display driver 117, the operation input detector 118, and the wireless communication unit 119 are connected to each other via a system bus BUS. Consequently, the CPU 113 is capable to access the ROM 114, the RAM 115, and the HDD 116, to control the display of various types of information on the display 111 via the display driver 117, to control the transmission and reception of various types of information (data) to and from the radiation generator 120 and the electronic cassette 40 via the wireless communication unit 119. Further, the CPU 113 is capable to grasp states of operation by a user with respect to the operation panel 112 via the operation input detector 118.

The radiation generator 120 is equipped with the radiation source 121, a wireless communication unit 123 that transmits and receives various types of information (data) such as the exposure conditions to and from the console 110, and a radiation source controller 122 that controls the radiation source 121 based on the received exposure conditions.

The radiation source controller 122 also includes a microcomputer and stores the received exposure conditions and so forth. The exposure conditions received from the console 110 include information such as tube voltage, tube current and the like. The radiation source controller 122 causes the radiation source 121 to apply the radiation X based on the received exposure conditions.

When capture of radiographic images is executed by the electronic cassette 40, if a bias voltage is continuously applied to the sensor portions 13 of the detection pixels 32A, any charge that has been photo-electrically converted is accumulated in the detection pixels 32A. As a result, charge leakage (blooming) or generation of induced charge due to floating capacitance occurs, which may cause deterioration in the quality of captured image.

Figure 9:
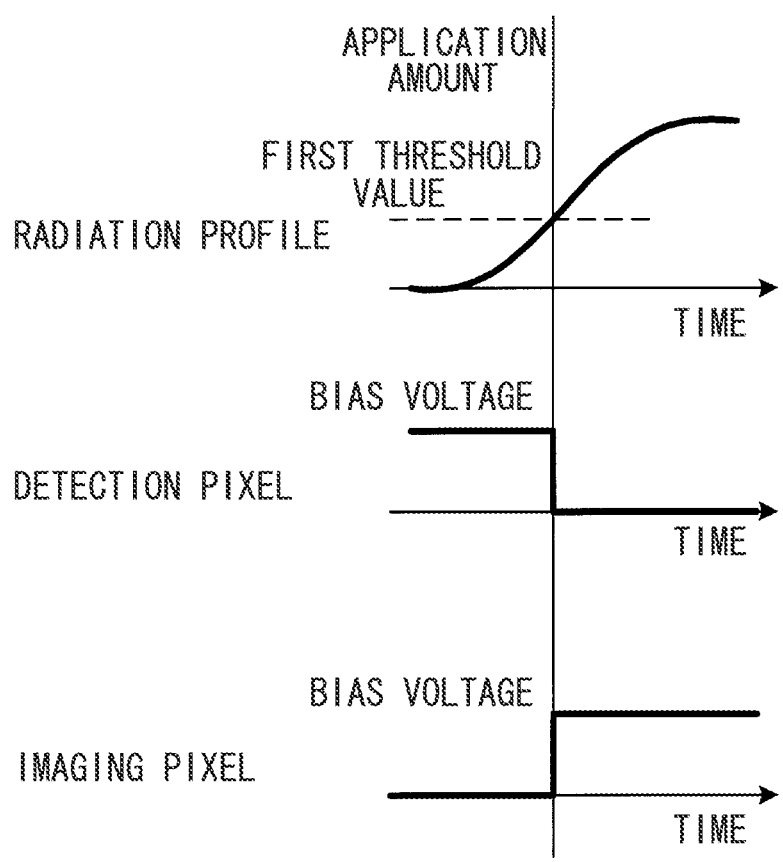
FIG. 9 is a waveform diagram for explanation of a bias switching function according to exemplary embodiments.

Therefore, in the electronic cassette 40 of the present exemplary embodiment, as shown in FIG. 9, a bias switching function is provided which effects control such that: prior to radiographic image capture, a bias voltage is applied to the sensor portions 13 of the detection pixels 32A and a bias voltage is not applied to the sensor portions 13 of the imaging pixels 32B (referred to below as a first state); and when the radiation X application amount has reached a predetermined first threshold value, a bias voltage is not applied to the sensor portions 13 of the detection pixels 32A and a bias voltage is applied to the sensor portions 13 of the imaging pixels 32B (referred to below as a second state). The bias switching function does not apply bias voltage to the sensor portions 13 of the imaging pixels 32B prior to radiographic image capture in order to prevent generation of dark current in the imaging pixels 32B.

In the electronic cassette 40 of the present exemplary embodiment, a predetermined value is applied as the first threshold value that indicates the initiation of radiation X application when the radiation application amount reaches the first threshold value or greater. However exemplary embodiments are not limited thereto, and configuration may be made by employing another value greater than the threshold value used for detecting initiation of application of radiation X.

Figure 10:
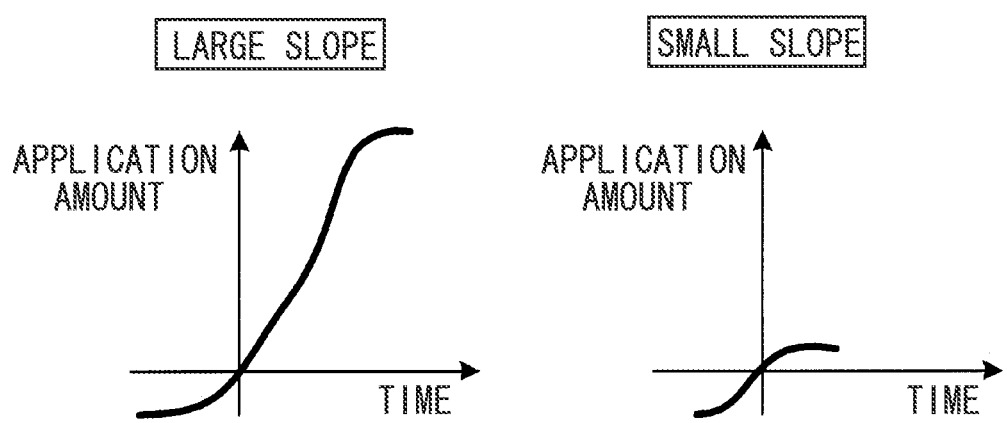
FIG. 10 shows two waveform diagrams for explanation of the bias switching function.

In the electronic cassette 40 according to the present exemplary embodiment, as shown in FIG. 10, the bias switching function is actuated when the slope of increase in radiation X application amount (the rate of increase) reaches a predetermined second threshold value or greater. This is because, the smaller the slope of increase in radiation X application amount is, the smaller the amount of blooming and generation of induced charge is, and the actuation of the bias switching function is not required. Thus, it is possible to prevent heat from the electronic cassette 40 and power consumption of the electronic cassette 40 by avoiding unnecessary execution of the bias switching function.

Generally, the amount of radiation application is made significantly smaller in capture of a radiographic video image than that in capture of still images (at about 1/100 to 1/1000) for the reasons such that there is comparatively less requirement for high quality for a radiographic video image than for still images, or in order to reduce the radiation dose to the subject. Consequently, configuration may be made such that the bias switching function is not actuated during capture of a video image.

Next, the operation of the imaging system 104 will be described.

Figure 11:
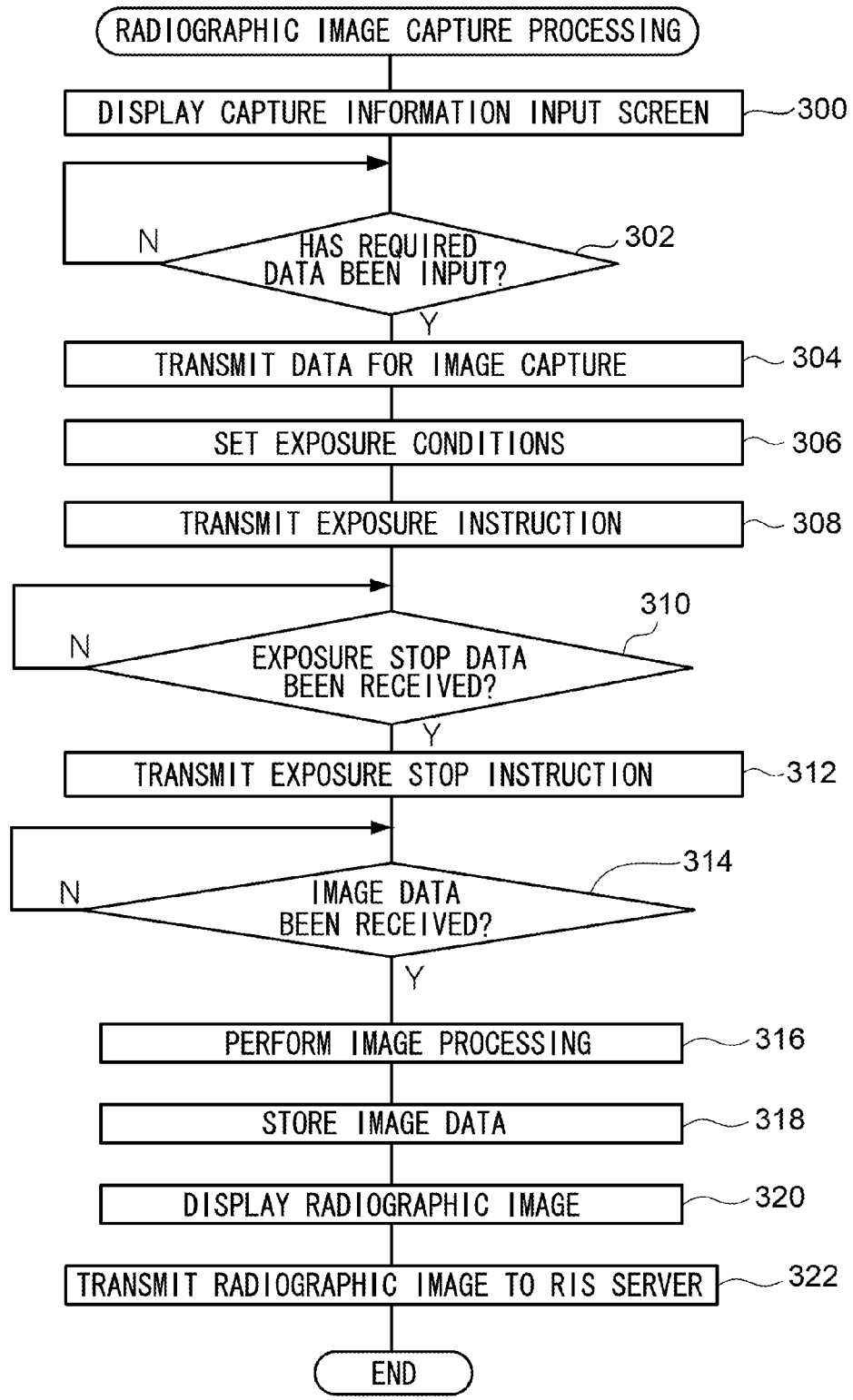
FIG. 11 is a flow chart illustrating the flow of processing in a radiographic image capture program according to exemplary embodiments.

First, the operation of the console 110 when capturing a radiographic image will be described with reference to FIG. 11. FIG. 11 is a flowchart showing a flow of processing by a radiographic image capturing program that is executed by the CPU 113 of the console 110 after an instruction to execute the program has been input via the operation panel 112. This program is stored in advance in a predetermined region of the ROM 114.

In step 300 of FIG. 11, the CPU 113 controls the display driver 117 so as to cause the display 111 to display a predetermined capture information input screen. In the next step 302, the CPU 113 waits for the input of predetermined information.

FIG. 12 shows an example of the capture information input screen that is displayed on the display 111 by the processing of step 300. As shown in FIG. 12, a message prompting a user (radiographer) to input the name of a subject on which radiographic imaging is to be performed, the imaging target site, the posture during imaging, and the exposure conditions of the radiation X during imaging (in the present exemplary embodiment, the tube voltage and the tube current when emitting the radiation X), and input fields for inputting these items of information are displayed in the capture information input screen.

After the capture information input screen shown in FIG. 12 is displayed on the display 111, the user may input the name of the subject serving as the imaging target, the imaging target site, the posture during imaging, and the exposure conditions into the corresponding input fields via the operation panel 112.

The user may then enter the radiographic imaging room 180 with the subject. In order to perform image capturing in a standing or lying position, after the electronic cassette 40 has been held respectively by the holding unit 162 of the standing position stand 160 or the holding unit 166 of the lying position table 164 and the radiation source 121 has been positioned in a corresponding position, the user performs positioning of the subject at a specific imaging position. In a case of performing radiographic image capture with the electronic cassette 40 not held by a holding unit, such as when the imaging target site is a region of an arm or leg, the user performs positioning of the subject, the electronic cassette 40 and the radiation source 121 in a state enabling imaging of the imaging target site.

The user may then exit the radiographic imaging room 180, and selects the INPUT COMPLETE button displayed in the vicinity of the bottom edge of the capture information input screen via the operation panel 112. The determination in step 302 is affirmative when the use has selected the INPUT COMPLETE button, and processing transitions to step 304.

At step 304, the data input to the capture information input screen (referred to below as data for image capture) is transmitted to the electronic cassette 40 using the wireless communication unit 119. In the next step 306, the exposure conditions included in the data for image capture is transmitted to the radiation generator 120 using the wireless communication unit 119 and the exposure conditions are set in the radiation generator 120. The radiation source controller 122 of the radiation generator 120 performs preparation for exposure according to the received exposure conditions.

In the next step 308, the CPU 113 transmits instruction data instructing the start of exposure to the radiation generator 120 via the wireless communication unit 119.

In response to the instruction data, the radiation source 121 starts emitting radiation X with the tube voltage and tube current corresponding to the exposure conditions that the radiation generator 120 has received from the console 110. Radiation X emitted from the radiation source 121 reaches the electronic cassette 40 after passing through the subject.

The cassette controller 58 of the electronic cassette 40 acquires the radiation application amount data using the radiation application amount acquisition function, and waits until the radiation application amount expressed by the acquired radiation application amount data reaches or exceeds the first threshold value serving as the value for detecting when radiation application has started. After radiographic image capture operation has started, the electronic cassette 40 stops the image capture operation when the elapsed duration since the start of radiation X application has reached a duration predetermined as the radiation X application duration (referred to below as the "application stop duration"), and transmits exposure stop data to the console 110.

The console 110 waits for receipt of the information of exposure stop data at the next step 310. After receipt of the irradiation stop data, the console 110 transmits instruction data instructing termination of irradiation of radiation X to the radiation generator 120 using the wireless communication unit 119 at the next step 312. In response to this, the radiation source 121 stops irradiation of radiation X.

After the radiographic image capture operation has stopped, the electronic cassette 40 transmits image data obtained by the image capture to the console 110.

The consol 110 waits at the next step 314 until the image data is received from the electronic cassette 40. At the next step 316, the missing pixel interpolation processing that has been described above is performed on the received image data before executing image processing for performing various types of correction such as shading correction.

In the next step 318, the image data that has been subject to image processing (referred to below as "corrected image data") is stored in the HDD 116. In the next step 320, the display driver 117 is controlled so as to display on the display 111 a radiographic image expressed by the corrected image data, for the user to perform verification or the like.

At the next step 322, the consol 110 transmits the corrected image data using the in-hospital network 102 to the RIS server 150, after which the radiographic image capture program is ended. The corrected image data transmitted to the RIS server 150 is stored in the database 150A, so that a doctor may read the captured radiographic image and perform diagnostics.

Explanation follows regarding operation of the electronic cassette 40, with reference to FIG. 13. FIG. 13 is a flow chart illustrating the flow of processing of a cassette image capture program executed by the CPU 58A of the cassette controller 58 in the electronic cassette 40 when data for image capture is received from the console 110. The program is pre-stored in a specific region of the memory 58B.

At step 400 of FIG. 13, the cassette controller 58 controls the connection states of the switch 72A and the switch 72B to achieve the first state. In the next step 402, the radiation application amount data is acquired using the radiation application amount acquisition function. The acquired radiation application amount data is stored in the memory 58B at the next step 404. Determination is made at the next step 406 as to whether or not the radiation application amount expressed by the acquired data is the first threshold value or greater. The processing returns to step 402 if the determination is negative. If the determination is affirmative, this is interpreted as meaning that irradiation of radiation X from the radiation source 121 has started, and the processing continues to step 408.

At step 408, the slope of increase in radiation application amount is derived from the radiation application amounts that is stored in the memory 58B as a result of the processing in step 404. Determination is made at step 410 as to whether or not the derived slope is the second threshold value or greater. The processing proceeds to step 412 when the determination is affirmative.

At step 412, the cassette controller 58 controls the connection states of the switch 72A and the switch 72B to achieve the second state, and the processing proceeds to step 416.

However, if the determination at step 410 is negative, the processing transitions to step 414 in which the cassette controller 58 effects control of setting the connection state of the switch 72A such that a bias voltage is applied to the sensor portions 13 of the imaging pixels 32B, and then the processing proceeds to step 416.

The radiographic image capture operation is started at step 416. Determination is then made at the next step 418 as to whether or not the elapsed duration since the start of radiation X application has reached the application stop duration. The processing proceeds to step 420 if the determination is negative.

At step 420, determination is made as to whether or not the bias voltage is being applied to the sensor portions 13 of the detection pixels 32A, and if the determination is negative, the processing returns to step 418. However, if the determination is affirmative, the processing proceeds to step 422 and the radiation application amount data is acquired with the radiation application amount acquisition function.

At the next step 424, the radiation application amounts acquired by the processing of step 422 are accumulated. At the next step 426, determination is made as to whether or not the accumulated radiation application amount at that time is greater than the first threshold value, and also is equal to or greater than a third threshold value serving as a threshold value for determining termination of bias voltage application to the sensor portions 13 of the detection pixels 32A. The processing proceeds to step 428 if the determination is affirmative.

At step 428, the cassette controller 58 effects control of disconnecting the switch 72B in order to terminate the application of the bias voltage to the sensor portions 13 of the detection pixels 32A, and the processing returns to step 418. Note that if the determination is negative at step 426, the processing returns to step 418 without performing any processing.

The point at which the determination at step 418 is affirmative is taken as being when the accumulated radiation X application amount has reached the level to stop the irradiation of radiation X, and the processing proceeds to step 430.

At step 430, the image capture operation that has been started by the processing of step 416 is stopped. At the next step 432, the irradiation stop data is transmitted to the console 110 using the wireless communication unit 60.

At the next step 434, the cassette controller 58 controls the gate line driver 52 so as to output an ON signal from the gate line driver 52 to each of the gate lines 34 in sequence one line at a time, thereby switching on each of the thin-film transistors 10 connected to each of the gate lines 34 in sequence one line at a time.

In the radiation detector 20, when each of the thin-film transistors 10 connected to each of the gate lines 34 is switched on by one line at a time, the charge accumulated in each of the capacitors 9 flows out as an electrical signal to each of the data lines 36 in sequence by one line at a time. The electrical signals flowing out to each of the data lines 36 are converted into digital image data by the first signal processor 54 and then stored in the image memory 56.

The cassette controller 58 reads the image data stored in the image memory 56 at step 434, and after the cassette controller 58 has transmitted the read image data to the console 110 using the wireless communication unit 60 at the next step 436, the cassette image capture program is ended.

In the cassette image capture program, if the slope of increase in radiation X application amount detected by the detection pixels 32A in the first state is less than the second threshold value, and the radiation application amount is equal to or greater than the third threshold value, which is greater than the first threshold value, as shown for example in FIG. 14, due to the processing in step 428, the application of the bias voltage to the sensor portions 13 of the detection pixels 32A is terminated with a slight delay from the start of bias voltage application to the sensor portions 13 of the imaging pixels 32B. Consequently, it is possible to achieve a certain level of effect of preventing deterioration of image quality, which may be caused by blooming or generation of induced charge due to floating capacitance.

In the electronic cassette 40 of the present exemplary embodiment, as shown in FIG. 7, the radiation detector 20 is installed such that radiation X are applied to the TFT substrate 30 side of the electronic cassette 40.

As shown in FIG. 15, in a case in which the radiation detector 20 is configured as being applied radiation from the side on which the scintillator 8 is formed, and the radiographic image is read by the TFT substrate 30 disposed on the reverse side of the surface applied with radiation, namely when the radiation detector 20 employs a Penetration Side Sampling (PSS) method, the top surface of the scintillator 8 shown in FIG. 15 (i.e., the surface at the opposite side to the TFT substrate 30) emits light with higher intensity. However, in a case in which the radiation detector 20 is configured as being applied radiation from the TFT substrate 30 side and radiographic images are read by the TFT substrate 30 disposed at the side on which radiation is applied, namely when the radiation detector 20 employs an Irradiation Side Sampling (ISS) method, radiation that has passed through the TFT substrate 30 is incident to the scintillator 8 and the TFT substrate 30 side of the scintillator 8 emits light with higher intensity. Each of the sensor portions 13 provided to the TFT substrate 30 generates charges due to the light generated in the scintillator 8. Accordingly, the radiation detector 20 achieves a higher resolution in captured radiographic images in a case of employing a PSS method than a case of employing an ISS method since the position of the scintillator 8 which emits light with most intense is closer to the TFT substrate 30.

Further, since the photoelectric conversion layer 4 of the radiation detector 20 is formed from an organic photoelectric conversion material, radiation is barely absorbed by the photoelectric conversion layer 4. Therefore, the radiation detector 20 of the present exemplary embodiment is capable of preventing deterioration in sensitivity to radiation even though an ISS method is employed and radiation passes through the TFT substrate 30, since the amount of radiation absorbed by the photoelectric conversion layer 4 is smaller. As described above, in an ISS method, the radiation passes through the TFT substrate 30 to reach the scintillator 8. However, configuring the photoelectric conversion layer 4 of the TFT substrate 30 from an organic photoelectric conversion material is suitable for an ISS method, since there is hardly any radiation absorption in the photoelectric conversion layer 4 and it is possible to reduce radiation attenuation to a small amount.

The film forming of both the amorphous oxide configuring the active layer 17 of the thin-film transistors 10 and the organic photoelectric conversion material configuring the photoelectric conversion layer 4 are possible at low temperature. The substrate 1 may accordingly be made from plastic resin, aramid or bionanofibers, having low absorptivity to radiation. Since the thus formed substrate 1 achieves small amount of radiation absorption, sensitivity to radiation may be prevented from deteriorating even when radiation passes through the TFT substrate 30 due to employing an ISS method.

Further, as shown in FIG. 7, the radiation detector 20 is attached to the top plate 41B inside the housing 41 so that the TFT substrate 30 is disposed at the top plate 41B side. In this case, if the substrate 1 is formed from a plastic resin, aramid or bionanofibers, having high rigidity, the top plate 41B of the housing 41 may be formed thinner since the rigidity of the radiation detector 20 itself is high. When the substrate 1 is formed from a plastic resin, aramid or bionanofibers with high rigidity, the radiation detector 20 is also provided with flexibility and will not easily damaged even when an impact is applied to the imaging region 41A.

As explained in detail above, the present exemplary embodiment effects control of transitioning from the first state in which a bias voltage is applied to the detection pixels to the second state in which the bias voltage is not applied to the detection pixels when the radiation application amount detected by the detection pixels has reached the first threshold value or greater. Therefore, it is capable of preventing deterioration in quality of captured images caused by accumulated charges in the detection pixels.

In the present exemplary embodiment, the first state is a state in which a bias voltage is applied to the detection pixels and a bias voltage is not applied to the imaging pixels, and the second state is a state in which a bias voltage is not applied to the detection pixels and a bias voltage is applied to the imaging pixels. As a result, it is capable of reducing the impact of dark current in the imaging pixels and further preventing deterioration in quality of captured image.

Further, the present exemplary embodiment effects the above control if the slope of increase in radiation application amount detected by the detection pixels in the first state is the second threshold value or greater. Therefore, it is possible to avoid execution of unnecessary processing.

In particular, the present exemplary embodiment effects the above control if the slope of increase in radiation application amount detected by the detection pixels in the first state is less than the second threshold value and the radiation application amount is equal to or greater than the third threshold value that is greater than the first threshold value. Therefore, it is capable of more reliably preventing deterioration in quality of captured image caused by accumulated charges in the detection pixels.

Since plural of the detection pixels are disposed between the plural imaging pixels the present exemplary embodiment, the effect of the present invention may be more fully appreciated.

Second Exemplary Embodiment

Detailed explanation follows regarding a second exemplary embodiment of the present invention. Since the imaging systems 104 according to the second exemplary embodiment are configured similarly to the first exemplary embodiment, further explanation thereof is omitted. The operation of a console 110 when capturing an radiographic image according to the second exemplary embodiment is also similar to that in the first exemplary embodiment and, therefore, further explanation thereof will also be omitted.

Explanation follows regarding the operation of the electronic cassette 40 according to the second exemplary embodiment, with reference to FIG. 16. FIG. 16 is a flow chart illustrating the flow of processing in a cassette image capture program executed by a CPU 58A of the cassette controller 58 of the electronic cassette 40 after data for image capture is received from the console 110. The cassette image capture program is pre-stored in a specific region of the memory 58B. Steps in FIG. 16 which are similar to that of FIG. 13 are given the same step numbers as in FIG. 13 and further explanation thereof is omitted.

In step 409 of FIG. 16, determination is made, based on received data for image capture, as to whether or not there is a requirement to perform transition from the first state to the second state of the bias voltage application to the sensor portions 13 of the radiation detector 20. Note that in this case, the determination of whether or not the transition to the second state is required is made by predicting the slope of increase in radiation X application amount based on the exposure conditions of radiation X for the image capture (i.e., the tube voltage and tube current for exposure of radiation X) included in the data for image capture, and determining whether or not the slope is equal to or greater than the second threshold value. However, embodiments are not limited thereto. For example, configuration may be made such that data indicating whether the type of capturing is video image capture or still image capture may be included in the data for image capture, and the transition to the second state may be determined if still image capture is to be performed.

At step 411, determination is made as to whether or not the result of the processing of step 409 is that a transition to the second state is required. If the determination is affirmative, the processing proceeds to step 412, and if the determination is negative, the processing proceeds to step 414.

As described above, the present exemplary embodiment not only exhibits substantially the same advantageous effects as in the first exemplary embodiment, but also determines whether or not effecting control of transitioning to the second state based on the data for image capture expressing the conditions for radiographic image capture. Therefore, the present exemplary embodiment may more easily and reliably avoid executing unnecessary processing than in a case of determining whether or not effecting control of transitioning to the second state based on the slope of increase in the radiation application amount.

While exemplary embodiments are described above, the technical scope is not limited thereto. Various modifications and improvements may be made to the above exemplary embodiments within a range not departing from the spirit of the invention, and embodiments including such modifications and improvements are also included in the technical scope of the present invention.

The above exemplary embodiments do not limit the invention according to the claims, and not all of the features explained in the exemplary embodiments necessarily essential for the solution of the invention. Various levels of invention are included in the exemplary embodiments, and various levels of invention may be obtained by appropriately combining plural elements disclosed herein. Where one or more of the elements are omitted from the total configuration of the exemplary embodiments, this configuration from which one or more of the elements have been omitted may also fall within the scope of the invention as long as the advantageous effects are obtained.

Figure 17A:
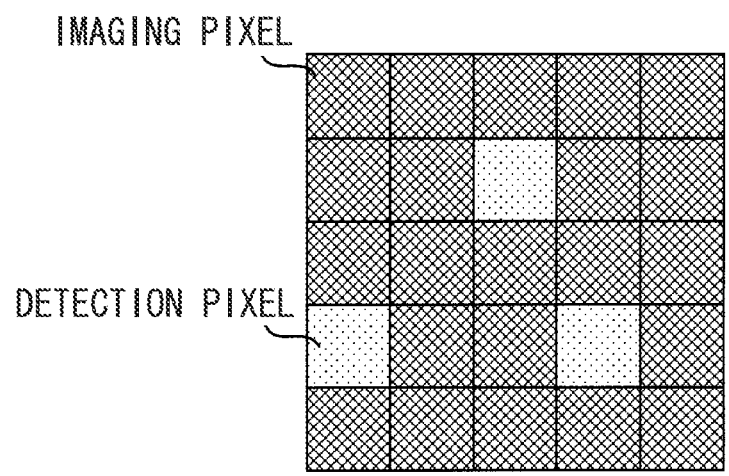
FIGS. 17A and 17B are plan views illustrating other examples of detection pixel arrangements.
Figure 17B:
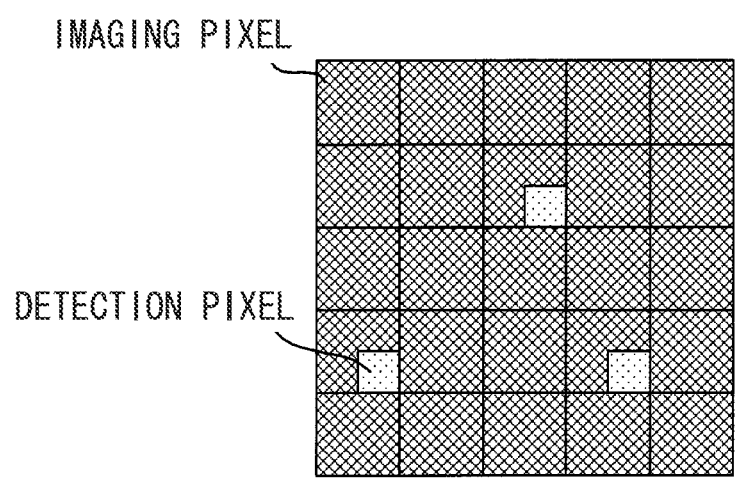

For example, explanation has been given in each of the exemplary embodiments of cases in which some of the imaging pixels 32B are employed as the detection pixels 32A, as shown in FIG. 17A. However, embodiments are not limited thereto. For example, as shown in FIG. 17B, the detection pixels 32A formed by dividing a portion of the sensor portion of some of the imaging pixels 32B to serve as a region for detection of radiation application state. In such cases, the sensitivity of these imaging pixels 32B corresponding to positions where the detection pixels 32A are provided is reduced due to the surface area of such pixels become smaller. However, since these pixels can be still used for imaging, the quality of the radiographic images may be improved.

Figure 18:
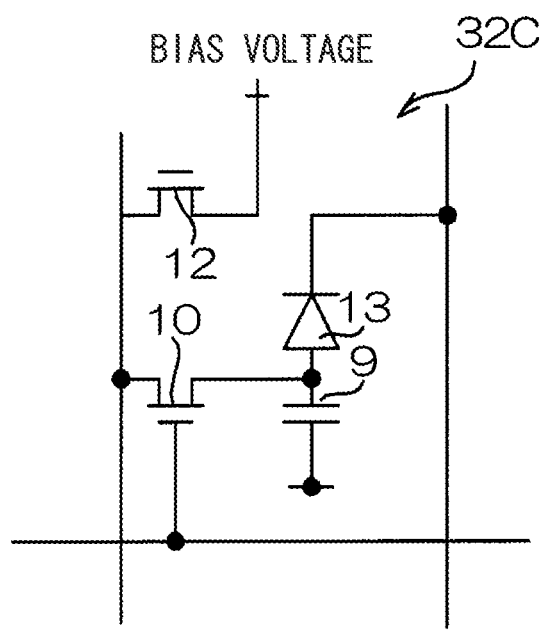
FIG. 18 is a circuit diagram illustrating another embodiment of a detection pixel.

Alternatively, as shown in FIG. 18, pixels 32C may be employed as the detection pixels 32A, in which a thin-film transistor 12 that is similar to the thin-film transistor 10 has been added to the imaging pixel 32B. In this configuration, a bias voltage is applied to the thin-film transistors 12 to detect the radiation application state. Further, in this configuration, light is illuminated onto the channel portion of the thin-film transistors 12 when radiation is applied, thereby raising the off current value of the thin-film transistors 12 and increasing the leak current. The start of radiation application, application amount, and the end of radiation application can be detected by monitoring this current value. Accordingly, similar advantageous effects to those of the above exemplary embodiments may also be exhibited in this configuration.

In the exemplary embodiments, the second state, in which the bias voltage applied to the detection pixels is lowered, is described as a state in which the bias voltage is not applied to the detection pixels. However, embodiments are not limited thereto. For example, the second state may be set as a state in which the detection pixels are applied with a second bias voltage that is lower than the bias voltage and higher than the voltage of the detection pixels in a state in which the bias voltage is not applied, or as a state in which a third bias voltage having reverse polarity with respect to the bias voltage is applied to the detection pixels. These configurations may also exhibit similar advantageous effects as those of the above exemplary embodiments.

Figure 19:
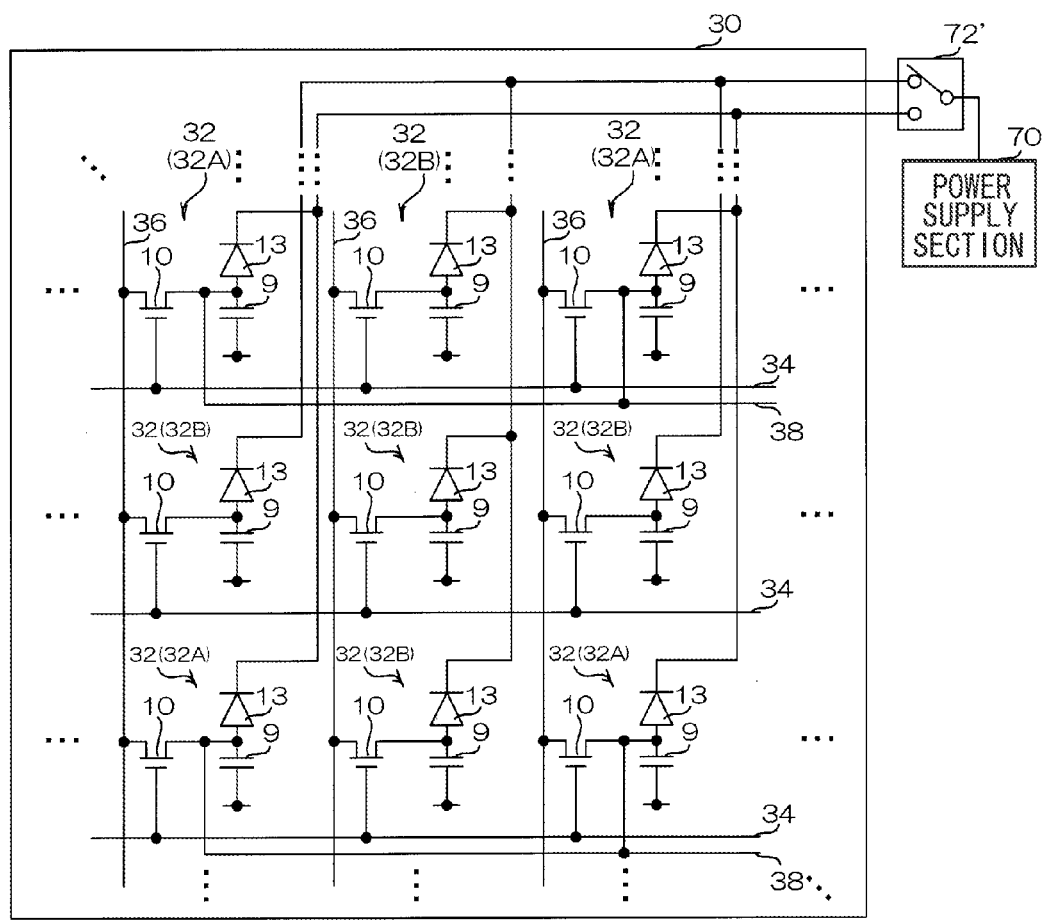
FIG. 19 is a plan view illustrating another example of a configuration of a radiation detector according to exemplary embodiments.

In the exemplary embodiments, as shown in FIG. 5, configurations has been described in which the sensor portions 13 of each of the detection pixels 32A and the sensor portions 13 of the imaging pixels 32B are each connected to the power supply section 70 by different lines, and it is possible to switch between application/non-application of voltage using the switch 72A and the switch 72B separately. However, embodiments are not limited thereto. For example, as shown in the example in FIG. 19, an embodiment may be made in which a switching section 72' having one input and two outputs is provided in place of the switch 72A and the switch 72B, and the transition from the first state to the second state is performed using the switching section 72'. In this case, control for the transition may be more easily performed than in the above exemplary embodiments.

In the above exemplary embodiments, the control of transitioning from the first state to the second state is executed in the electronic cassette 40. However, embodiments are not limited thereto. For example, the control of transitioning may be performed in the console 110. This configuration may also exhibit similar advantageous effects as those of the above exemplary embodiments.

In the above exemplary embodiments, some of the pixels 32 provided in the radiation detector 20 are employed as the detection pixels 32A. However, embodiments are not limited thereto. For example, the detection pixels 32A may be formed in a different layer to the pixels 32 and are stacked in the radiation detector 20. In this case, the radiographic image quality may be improved in comparison to the above exemplary embodiments since there is no missing pixel.

An organic CMOS sensor formed from a material containing an organic photoelectric conversion material may be employed in the photoelectric conversion layer 4 as the sensor portions 13 of the radiation detector 20. Further, an organic TFT array-sheet, in which organic transistors containing an organic material are arrayed as the thin-film transistors 10 on a flexible sheet, may be employed as the TFT substrate 30 of the radiation detector 20. An example of such an organic CMOS sensor is described in JP-A No. 2009-212377. An example of such an organic TFT array-sheet is described in the Nikkei Newspaper article published online (search date May 8, 2011) "The University of Tokyo develops "Ultra-flexible Organic Transistor"", Internet <URL: http://www.nikkei.com/tech/trend/article/g=96958A9C93819499E2EAE2E0E48DE2EAE3E3E0E2E3E2E2E2E2E2E2E2; p=9694E0E7E2E6E0E2E3E2E2E0E2E0>.

If a CMOS sensor is employed as the sensor portions 13 of the radiation detector 20, it is possible to perform high speed photoelectric conversion and to make the substrate thinner. As a result, there is an advantage that radiation absorption may be prevented in configurations employing an ISS method and that the radiation detector 20 may be suitability used in mammography imaging.

In the above exemplary embodiments, the sensor portions 13 are configured by including an organic photoelectric conversion material that generates charge by receiving light that has been generated in the scintillator 8. However, embodiments are not limited thereto, and the sensor portions 13 may be configured without including an organic photoelectric conversion material.

In the above exemplary embodiments, the case 42 containing components such as the cassette controller 58 and the power supply section 70 and the radiation detector 20 are disposed inside the housing 41 of the electronic cassette 40 such that both do not overlap with each other. However, embodiments are not limited thereto. For example, the cassette controller 58 and the power supply section 70 may be disposed so as to overlap with the radiation detector 20.

In the above exemplary embodiments, wireless communication is performed between the electronic cassette 40 and the console 110 and between the radiation generator 120 and the console 110. However, embodiments are not limited thereto and, for example, wired communication may be employed in either or both cases.

In the above exemplary embodiments, X-rays are employed as radiation. However, embodiments are not limited thereto, and another type of radiation, such as gamma-rays may be employed as radiation.

The configuration of the RIS 100 (see FIG. 1), the configuration of the radiography room (see FIG. 2), the configuration of the electronic cassette 40 (see FIG. 3 to FIG. 7), and the configuration of the imaging systems 104 (see FIG. 8) in the above exemplary embodiments are also merely examples. Obviously, sections not required may be omitted, new sections may be added and connection states may be changed within a range not departing from the spirit of the present invention.

The configuration of the data for image capture explained in the above exemplary embodiments is also merely an example. Obviously, data not required may be omitted and new data may be added within a range not departing from the spirit of the present invention.

The flow of processing of the programs explained in the above exemplary embodiments (see FIG. 11, FIG. 13, FIG. 16) are also merely examples. Obviously, steps not required may be omitted, new steps may be added, and the processing sequence may be changed within a range not departing from the spirit of the present invention.

The configuration of the capture information input screen explained in the above exemplary embodiments (see FIG. 12) is also merely an example. Obviously, data not required may be omitted and new data may be added within a range not departing from the spirit of the present invention.

What is claimed is:

1. A radiographic image capture device comprising:
    a radiation detector comprising a plurality of detection pixels configured to detect a radiation application state and a plurality of imaging pixels configured to capture a radiographic image;
    an application section that applies a bias voltage to each of the plurality of detection pixels and to each of the plurality of imaging pixels, the application section comprising a switching section that selectively switches a feed-destination of the bias voltage generated by a power supply section between the plurality of detection pixels and the plurality of imaging pixels; and
    a controller that effects control such that, when a radiation application amount detected by the detection pixels is equal to or greater than a first threshold value during a first state in which the bias voltage is applied to the plurality of detection pixels, the application section is caused to transition to a second state in which the bias voltage applied to the detection pixels is reduced,
    wherein the first state is a state in which the bias voltage is applied to the detection pixels and the bias voltage is not applied to the imaging pixels, and the second state is a state in which the bias voltage applied to the detection pixels is reduced and the bias voltage is applied to the imaging pixels.

2. The radiographic image capture device of claim 1, wherein the controller effects the control when a slope of increase in the radiation application amount detected by the detection pixels in the first state is equal to or greater than a second threshold value.

3. The radiographic image capture device of claim 2, wherein the controller effects the control when the slope of increase in the radiation application amount detected by the detection pixels in the first state is less than the second threshold value and the radiation application amount is equal to or greater than a third threshold value that is greater than the first threshold value.

4. The radiographic image capture device of claim 1, wherein the controller effects the control based on data for image capture expressing conditions for radiographic image capture.

5. The radiographic image capture device of claim 1, wherein the plurality of detection pixels are disposed between the plurality of imaging pixels.

6. The radiographic image capture device of claim 1, wherein each of the plurality of detection pixels is formed by adding a radiation detection thin-film transistor to one of the plurality of imaging pixels.

7. The radiographic image capture device of claim 1, wherein the plurality of detection pixels is respectively formed in some of the plurality of imaging pixels by dividing a region of a sensor portion of each imaging pixel to serve as a radiation application state detection region.

8. The radiographic image capture device of claim 1, wherein the second state is one of the following states:
    (a) a state in which a second bias voltage is applied to the plurality of detection pixels, wherein the second bias voltage is lower than the bias voltage and higher than a voltage applied to the plurality of detection pixels in a state in which the bias voltage is not applied;
    (b) a state in which the bias voltage is not applied to the detection pixels; or
    (c) a state in which a third bias voltage that has a reverse polarity with respect to the bias voltage is applied to the detection pixels.

9. The radiographic image capture device of claim 8, wherein:
    the second state is (b) the state in which the bias voltage is not applied to the detection pixels;
    the application section further comprises the power supply section that generates the bias voltage that is common for the plurality of detection pixels and the plurality of imaging pixels, and a switching section that selectively switches a feed-destination of the bias voltage generated by the power supply section to the plurality of detection pixels or the plurality of imaging pixels; and
    the controller causes transition from the first state to the second state by switching of the switching section.

10. The radiographic image capture device of claim 1, wherein each of the plurality of detection pixels is dispersedly disposed among the plurality of imaging pixels.

11. The radiographic image capture device of claim 1, wherein each of the plurality of detection pixels is disposed without being directly adjacent to each other, and is surrounded by the plurality of imaging pixels.

12. A radiographic image capture system comprising:
a radiographic image capture device comprising a radiation detector including a plurality of detection pixels configured to detect a radiation application state and a plurality of imaging pixels configured to capture a radiographic image, and an application section that applies a bias voltage to each of the plurality of detection pixels and to each of the plurality of imaging pixels, the application section comprising a switching section that selectively switches a feed-destination of the bias voltage generated by a power supply section between the plurality of detection pixels and the plurality of imaging pixels; and
a controller that effects control such that, when a radiation application amount detected by the plurality of detection pixels is equal to or greater than a first threshold value during a first state in which the bias voltage is applied to the detection pixels, the application section is caused to transition to a second state in which the bias voltage applied to the detection pixels is reduced,
wherein the first state is a state in which the bias voltage is applied to the detection pixels and the bias voltage is not applied to the imaging pixels, and the second state is a state in which the bias voltage applied to the detection pixels is reduced and the bias voltage is applied to the imaging pixels.

13. The radiographic image capture system of claim 12, wherein each of the plurality of detection pixels is dispersedly disposed among the plurality of imaging pixels.

14. The radiographic image capture system of claim 12, wherein each of the plurality of detection pixels is disposed without being directly adjacent to each other, and is surrounded by the plurality of imaging pixels.

15. A non-transitory computer readable program storage medium that stores a program that causes a radiographic image capture device to perform a processing, the radiographic image capture device including a radiation detector including a plurality of detection pixels configured to detect a radiation application state and a plurality of imaging pixels configured to capture a radiographic image, and an application section that applies a bias voltage to each of the plurality of detection pixels and to each of the plurality of imaging pixels, the processing comprising:
determining whether or not a radiation application amount detected by the detection pixels during a first state in which the bias voltage is applied to the detection pixels is equal to or greater than a first threshold value; and
controlling the application section to transition to a second state in which the bias voltage applied to the detection pixels is reduced when it is determined that the application amount is equal to or greater than the first threshold,
wherein the first state is a state in which the bias voltage is applied to the detection pixels and the bias voltage is not applied to the imaging pixels, and the second state is a state in which the bias voltage applied to the detection pixels is reduced and the bias voltage is applied to the imaging pixels, and
the application section includes a switching section that selectively switches a feed-destination of the bias voltage generated by a power supply section between the plurality of detection pixels and the plurality of imaging pixels.

16. The non-transitory program storage medium of claim 15, wherein the controlling is performed when a slope of increase in the radiation application amount detected by the detection pixels in the first state is equal to or greater than a second threshold value.

17. The non-transitory program storage medium of claim 16, wherein the controlling is performed when the slope of increase in the radiation application amount detected by the detection pixels in the first state is less than the second threshold value and the radiation application amount is equal to or greater than a third threshold value that is greater than the first threshold value.

18. The non-transitory program storage medium of claim 15, wherein the controlling is performed based on data for image capture expressing conditions for radiographic image capture.

19. The non-transitory program storage medium of claim 15, wherein the second state is one of the following states:
(a) a state in which the plurality of detection pixels are applied with a second bias voltage that is lower than the bias voltage and higher than a voltage of the plurality of detection pixels in a state in which the bias voltage is not applied;
(b) a state in which the bias voltage is not applied to the plurality of detection pixels; or
(c) a state in which a third bias voltage that has a reverse polarity with respect to the bias voltage is applied to the plurality of detection pixels.

20. The non-transitory program storage medium of claim 15, wherein each of the plurality of detection pixels is dispersedly disposed among the plurality of imaging pixels.

21. The non-transitory program storage medium of claim 15, wherein each of the plurality of detection pixels is disposed without being directly adjacent to each other, and is surrounded by the plurality of imaging pixels.

22. A radiographic image capture method for a radiation detector including a plurality of detection pixels configured to detect a radiation application state and a plurality of imaging pixels configured to capture a radiographic image, the method comprising:
determining whether or not a radiation application amount detected by the plurality of detection pixels during a first state, in which a bias voltage is applied to the plurality of detection pixels, is equal to or greater than a first threshold value; and
transitioning to a second state in which the bias voltage applied to the plurality of detection pixels is reduced when it is determined that the application amount is equal to or greater than the first threshold value,
wherein the first state is a state in which the bias voltage is applied to the plurality of detection pixels and the bias voltage is not applied to the plurality of imaging pixels, and the second state is a state in which the bias voltage applied to the plurality of detection pixels is reduced and the bias voltage is applied to the plurality of imaging pixels, and
a switching section selectively switches a feed-destination of the bias voltage generated by a power supply section between the plurality of detection pixels and the plurality of imaging pixels.

23. The method of claim 22, wherein the transitioning is performed when a slope of increase in the radiation application amount detected by the detection pixels in the first state is equal to or greater than a second threshold value.

24. The method of claim 23, wherein the transitioning is performed when the slope of increase in the radiation application amount detected by the detection pixels in the first state is less than the second threshold value and the radiation application amount is equal to or greater than a third threshold value that is greater than the first threshold value.

25. The method of claim 22, wherein the transitioning is performed based on data for image capture expressing conditions for radiographic image capture.

26. The method of claim 22, wherein the second state is one of the following states:
   (a) a state in which the plurality of detection pixels are applied with a second bias voltage that is lower than the bias voltage and higher than a voltage of the plurality of detection pixels in a state in which the bias voltage is not applied;
   (b) a state in which the bias voltage is not applied to the plurality of detection pixels; or
   (c) a state in which a third bias voltage that has a reverse polarity with respect to the bias voltage is applied to the plurality of detection pixels.

27. The method of claim 22, wherein each of the plurality of detection pixels is dispersedly disposed among the plurality of imaging pixels.

28. The method of claim 22, wherein each of the plurality of detection pixels is disposed without being directly adjacent to each other, and is surrounded by the plurality of imaging pixels.

* * * * *